(12) United States Patent
Dooley et al.

(10) Patent No.: US 7,718,185 B2
(45) Date of Patent: May 18, 2010

(54) INHIBITORS OF MELANOCYTE TYROSINASE AS TOPICAL SKIN LIGHTENERS

(75) Inventors: Thomas P. Dooley, Vestavia Hills, AL (US); Ernest V. Curto, Huntsville, AL (US)

(73) Assignee: MediQuest Therapeutics, Inc., Bothell, WA (US)

( * ) Notice: Subject to any disclaimer, the term of this patent is extended or adjusted under 35 U.S.C. 154(b) by 50 days.

(21) Appl. No.: 12/206,334

(22) Filed: Sep. 8, 2008

(65) Prior Publication Data

US 2009/0023793 A1    Jan. 22, 2009

Related U.S. Application Data

(60) Division of application No. 11/075,922, filed on Mar. 10, 2005, now abandoned, which is a continuation of application No. 09/795,683, filed on Feb. 28, 2001, now abandoned.

(60) Provisional application No. 60/185,610, filed on Feb. 29, 2000.

(51) Int. Cl.
    *A61K 8/02*    (2006.01)
    *A01N 43/00*   (2006.01)
(52) U.S. Cl. ...................... 424/401; 514/183
(58) Field of Classification Search .................. 424/401
    See application file for complete search history.

(56) References Cited

U.S. PATENT DOCUMENTS 6,514,486 B1   2/2003   Tuloup et al.

FOREIGN PATENT DOCUMENTS

| JP | 5-124925 A | 5/1993 |
|---|---|---|
| JP | 09323955 | 12/1997 |
| WO | WO 99/22707 | 5/1999 |

OTHER PUBLICATIONS

"Inhibition of Melanin Synthesis by Cystamine in Human Melanoma Cells" by Qiu et al., The Society for Investigative Dermatology, Inc. (2000) pp. 21-27.
Chand P et al.: "Design and Synthesis of Benzoic Acid Derivatives as Influenza Neuraminidase Inhibitors Using Structure-based Drug Design", Journal of Medicinal Chemistry, American Chemical Society, Washington, US, vol. 40, No. 25, 1997, pp. 4030-4052.
Chua-M-S et al: "Antitumor Benzothiazoles, 7. Synthesis of 2-(4-acylaminophenyl) Benzo-thiazoles and Investigations into the Role of Acetylation in the Antitumor Activities of the Parent Amines", Journal of Medicinal Chemistry, American Chemical Society, Washington, US, vol. 42, No. 3, Feb. 11, 1999, pp. 381-392.
Sicardi S M et al: "Mutagenic and Analgesic Activities of Aniline Derivatives", Journal of Pharmaceutical Sciences, vol. 80, No. 8, 1991, pp. 761-764.
Database Medline US National Library of Medicine (NLM), Bethesda, MD, US; Aug. 1983, Trennery P N et al: "The metabolism of Thioacetanilide in the Rat" XP002460434.

*Primary Examiner*—Sreeni Padmanabhan
*Assistant Examiner*—Layla Soroush
(74) *Attorney, Agent, or Firm*—Connolly Bove Lodge & Hutz LLP

(57) ABSTRACT

Methods and formulations are provided to reduce pigmentation in skin, using an array of compounds selected from benzimidazoles, phenylthioureas, phenyltiols, phenylamines, bi- and multicyclic phenols, thiopheneamines, and benzothiamides. The compounds preferably inhibit pigment synthesis in melanocytes through the tyrosinase pathway. The methods can be used for lightening skin, and for treating uneven skin complexions which result from hyperpigmentation-related medical conditions such as melasma, age spots, freckles, ochronosis, and lentigo. The compounds can be used medically or cosmetically.

10 Claims, No Drawings

INHIBITORS OF MELANOCYTE TYROSINASE AS TOPICAL SKIN LIGHTENERS

CROSS REFERENCE TO PRIOR APPLICATIONS

This application is a divisional of U.S. patent application Ser. No. 11/075,922, filed Mar. 10, 2005, now abandoned which is a continuation of U.S. patent application Ser. No. 09/795,683, filed Feb. 28, 2001, now abandoned and further claims priority to U.S. Provisional Patent Application No. 60/185,610, filed Feb. 29, 2000, the entire disclosures of which are incorporated herein by reference in their entirety.

FIELD OF THE INVENTION

The present invention relates to compounds and methods for inhibiting the activity of melanocyte tyrosinase in mammalian skin, in order to reduce the expression and production of skin pigmentation, and thereby lighten the color of mammalian skin.

BACKGROUND OF THE INVENTION

Melanogenesis is the process of production and subsequent distribution of melanin by melanocytes within the skin and hair follicles [1, 2]. Melanocytes have specialized lysosome-like organelles, termed melanosomes, which contain several enzymes that mediate the production of melanin. The copper-containing enzyme tyrosinase catalyzes the oxidation of the amino acid tyrosine into DOPA and subsequently DOPA-quinone. At least two additional melanosomal enzymes are involved in the eumelanogenesis pathway that produces brown and black pigments, including TRP-1 (DHICA oxidase), and TRP-2 (DOPAchrome tautomerase). Depending on the incorporation of a sulfur-containing reactant (e.g. cysteine or glutathione) into the products, the melanogenesis pathway diverges to produce pheomelanins (amber and red pigments).

The perceived color of skin and hair is determined by the ratio of eumelanins to pheomelanins, and in part on blood within the dermis. The balance in skin hue is genetically regulated by many factors, including but not limited to: (a) the levels of expression of tyrosinase, TRP-2, and TRP-1; (b) thiol conjugation (e.g. with glutathione or cysteine) leading to the formation of pheomelanins; (c) the α-melanocyte-stimulating hormone (α-MSH) and melanocortin receptor, which is coupled to the adenylate cyclase/protein kinase A pathway; [15] (d) the product of the agouti locus, agouti signal protein, which has been documented to down-regulate pigmentation of hair melanocytes in rodents; [16] and (e) yet unknown mechanisms that regulate the uptake and distribution of melanosomes in recipient epidermal and hair matrix keratinocytes. [2, 13, 14]

Abnormalities of human skin pigmentation occur as a result of both genetic and environmental factors. Exposure of skin (especially Caucasian) to ultraviolet radiation, particularly in the UVB (i.e. intermediate) wavelengths, upregulates synthesis of melanocyte tyrosinase resulting in increased melanogenesis and thus tanning. However, acute or persistent UVB exposure can result in the formation of hyperpigmented lesions or regions of skin, including malignant melanoma skin cancer. [17] Both actinic damage and constitutional abnormalities can produce affected regions such as melasma, age spots, liver spots, freckles and other lentigenes. [3, 18, 19]

Vitiligo is the converse of hyperpigmentation, in which cutaneous melanocytes are either ablated or fail to produce sufficient pigment. [17, 18, 20] Although it would be desirable to restore lost pigmentation in vitiligo-affected skin with topical therapies, this has proven to be quite difficult to accomplish in a high proportion of subjects. As an alternative to PUVA therapy or cosmetic camouflage with dihydroxyacetone sunless-tanning lotions, [18] one might reduce the normal pigmentation of the unaffected skin to reduce contrast. Furthermore, a global market demand has developed for skin-lightening agents as "vanity" cosmeceutical products, because lighter skin color is preferred by some dark-skinned individuals in many countries and races, for psychological or sociological reasons. [4, 5]

Some purportedly "active" or "functional" agents for lightening skin color (e.g. arbutin, kojic acid, niacinamide, licorice, magnesium ascorbyl phosphate, among others) have not been demonstrated yet to be clinically efficacious when critically analyzed in carefully controlled studies [5, 6, 25]. The U.S. FDA-approved pharmaceutical products containing 2-4% hydroquinone ("HQ") are minimally to moderately efficacious. However, HQ has been demonstrated to be cytotoxic to cultured mammalian melanocytes, and mutagenic in *Salmonella* and mammalian Chinese hamster V79 cells [3-6, 10, 11, 25]. HQ appears to be an important intermediate in the bioactivation of the carcinogen benzene [12]. Although it has been repeatedly asserted in the dermatologic literature for many years, without substantiation, that HQ is an inhibitor of tyrosinase, this compound is not an effective inhibitor of the mammalian enzyme [5, 6, 25]. Hydroquinone's in vitro mechanism of action appears to be primarily a melanocytic cytotoxic effect. Its clinical mechanism of action on whole skin remains uncertain.

In view of these biochemical disadvantages of the standard skin bleaching agent, HQ, it is highly desirable to identify other compounds with improved efficacy and safety characteristics. Methyl gentisate ("MG"), the methyl ester of gentisic acid (GA; 2,5-dihydroxybenzoic acid), is a moderately potent inhibitor of melanin accumulation in a murine melanocyte cell culture primary screen [6, 25]. GA is a natural product from the root of the genus *Gentiana*, named after Gentius, an Illyrian (Greco-Roman) king of the $2^{nd}$ century B.C., said to have first discovered the medicinal properties of the plant [7]. The sodium salt of GA is thought to be an analgesic and an anti-inflammatory agent. GA is a ubiquitous metabolite, produced not only by plants, but also by *Penicillium patulum* and *Polyporus tumulosus*, and is excreted into the urine of mammals following ingestion of salicylates [8, 9]. MG and GA are simple phenolic compounds structurally similar to HQ, yet lacking the mutagenic activity of HQ [25]. MG has not been developed as a commercially available topical skin lightener product to date.

Two patent publications of Sansei Seiyaku also disclose a number of compounds, which allegedly are active as either tyrosinase inhibitors or as skin lightening agents, JP 5-124925 and JP 5-124922. The compounds are various benzimidazolethiols, but have not been developed as commercially available topical skin lightener products to date. In addition, phenylthiourea (PTU) has been reported as an inhibitor of tyrosinase, but has not been developed as a commercially available topical skin lightener product to date [30-32].

It is an object of this invention to provide methods and compositions for reducing pigmentation in skin from mammals, including humans.

Another object is to provide methods and compositions for reducing pigmentation of skin for cosmetic, beauty-enhancing, or esthetic effects.

It is another object to provide methods and compositions for treating hyperpigmentation-related medical conditions such as melasma, age spots, freckles, ochronosis, postinflammatory hyperpigmentation, lentigo, and other pigmented skin blemishes.

Another object of the present invention is to provide methods and compositions for inhibiting mammalian melanocyte tyrosinase, the rate-limiting enzyme in the production of melanin from tyrosine and DOPA.

Still another object of the invention is to provide methods and compositions to absorb ultraviolet radiation (UVR), and thus to protect skin from UVR and photoaging.

An additional object of the invention is to provide antioxidant compositions that protect skin from oxidative damage, and/or to prevent oxidative decomposition of product formulations.

Another object is to facilitate discovery of compounds that inhibit mammalian tyrosinase in cell-free extracts from mammalian melanocyte or melanoma cells, using either a colorometric DOPA oxidation or a radiolabeled tyrosine or DOPA substrate assay ($IC_{50} \leq 300$ μM).

Another object is to facilitate discovery of compounds that inhibit de novo pigment production (synthesis and/or accumulation) in cultured mammalian melanocyte or melanoma cells ($IC_{50} \leq 300$ μM).

Another object is to facilitate evaluation of compounds for toxicity in mammalian melanocyte, melanoma, or other cell cultures ($IC_{50} \leq 300$ μM.

Another object is to provide composition of matter and/or identity of compounds that are efficacious and/or exhibit reduced toxicity using one or more of the bioassays described in other objects, with biochemical characteristics equivalent to or superior to hydroquinone or methyl gentisate.

Another object is to provide active and/or functional compounds from diverse structural classes, including but not limited to the following examples: benzoimidazoles, phenylamines, phenylthioureas, phenols, and phenylthiols.

Still another object is to provide synthesis of derivatives of active and/or functional compounds of the invention, including by organic synthesis, combinatorial chemistry, medicinal chemistry, X-ray crystallography, rational drug design, and other methods.

Another object is to provide the use of formulations of the present invention for cosmetic, cosmeceutical, over-the-counter drug, and prescription drug products.

Another object is to provide formulations of the present invention for the purpose of reducing or preventing pigmentation in hair, albeit during the biosynthesis of hair, as a result of blocking pigment production within the melanocytes of hair follicles.

Another object is to provide the active and/or functional compounds of the present invention for use in inhibiting tyrosinase or tyrosinase-like enzymes from non-mammalian species, for instance for use in the food science industry for the inhibition of enzymatic browning.

Still another object is to provide the active and/or functional compounds of the present invention for use in inhibiting tyrosine hydroxylase enzymes, in order to reduce the biosynthesis of DOPA and/or catecholamines.

SUMMARY OF THE INVENTION

Several classes of compounds are provided that reduce or prevent the production of pigment by mammalian melanocytes. The compounds preferably inhibit the enzymatic activity of melanocyte tyrosinase, though some compounds control pigment production in melanocyte cells without being potent inhibitors of the enzyme. Therefore, the compounds can be used in applications wherein controlling or preventing the production of pigments in mammalian skin is desired. A few examples of such applications include:

1. As a vanity product, to lighten the skin of an individual, especially of dark skinned individuals;
2. To lessen the hue of pigmented skin blemishes such as freckles and age spots;
3. To diminish uneven pigmentation marks and surface color irregularities;
4. To treat hyperpigmentation-related medical conditions such as melasma, ochronosis, and lentigo;
5. To lighten hair pigmentation when applied to skin containing pigmented hair follicles;
6. To lessen postinflammatory hyperpigmentation resulting from trauma or invasive surgery from a face lift, laser treatment, or cosmetic surgery, and
7. To reduce skin pigmentation in normal skin adjacent to areas affected by vitiligo, thereby diminishing the contrast in color between normal and vitiligo affected skin.

Several classes of active skin lightening compounds have been discovered with which the present invention can be practiced. These compounds exhibit activity in the mammalian tyrosinase and/or melanocyte cell culture pigmentation assays, yet with minimal or no cytotoxicity. These compounds exhibit characteristics that are equivalent to or superior to the known standard skin-bleaching agent, hydroquinone, or the known standard tyrosinase inhibitor, methyl gentisate.

The compounds are typically applied topically to the skin wherein tyrosinase activity is sought to be reduced through a lotion or occlusive patch. The compounds can be spread over a larger area to produce an even skin tone fade, or they can be applied locally to skin blemishes and other localized conditions to minimize skin irregularities. Moreover, because most of the compounds are selective against melanocyte tyrosinase, the compounds can also be administered systemically by methods including oral, intradermal, transdermal, intravenous, and parenteral administrations. The product works by inhibiting the production of melanin in cells beneath the skin surface. Because the skin naturally renews itself every ca. 28 days, when the compounds of the present invention are administered old (differentiated) pigmented keratinocytes cells are gradually sloughed off and keratinocytes with less melanin are eventually brought to the surface giving the skin a lighter, more even toned complexion.

In a first principal embodiment the compounds of the present invention are benzimidazole and phenylthiourea related compounds represented by the following formula (I):

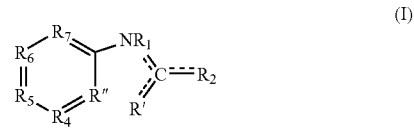

(I)

wherein:
1) $R_1$ is H or a valence for bonding,
2) $R_2$ is S, or SH;
3) one of the dotted lines ( - - - ) represents a bond;
4) $R_4$, $R_5$, $R_6$, and $R_7$ are independently $CR_8$, or N;
5) $R_8$ is (i) hydrogen, (ii) halogen, (iii) $NO_2$, (iv) —CN, (v) —$OR_{10}$, (vi) —$NHSO_2$—$C_{1-3}$alkyl, (vii) —NHCO—$C_{1-5}$ alkyl, (viii) oxime, (ix) hydrazine, (x) —$NR_9R_{10}$, (xi) $HSO_2$, (xii) $HSO_3$, (xiii) thio-$C_{1-5}$ alkyl, (xiv) $C_{1-5}$ acyloxy, (xv) $H_2PO_3$, (xvi) thiol, (xvii) —$COOR_9$, (xviii) $C_{1-5}$ alkynyl, or (xix) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy, 6) $R_9$ is hydrogen or $C_{1-3}$ alkyl;

7) $R_{10}$ is hydrogen, or $C_{1-5}$ alkyl optionally substituted with —OH;

8) R" is C or CH;

9) when R" is C:
  a) R' is $CR_8$, $C(R)_2$, N, or NH, and forms a bond with R";
  b) 1 or 2 of $R_5$ and $R_6$ are NH or $COR_{10}$ other than COH, the remainder of $R_4$, $R_5$, $R_6$, and $R_7$ being CH; and 10) when R" is CH, R' is $CH_3$ or $NH_2$.

In a second principal embodiment the compounds of the present invention are benzimidazole and phenylthiourea related compounds represented by the following formula (II):

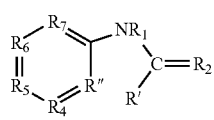

(II)

wherein:
1) $R_1$ is H;
2) $R_2$ is selenium;
3) R" is C or CH;
4) when R" is C, R' is $C(R_8)_2$ or $NR_3$, and forms a bond with R";
5) when R" is CH, R' is $CH_3$ or $NH_2$;
6) $R_4$, $R_5$, $R_6$, and $R_7$ are independently $CR_8$, or N;
7) $R_3$ is (i) substituted or unsubstituted alkyl, alkenyl, aryl, or heterocycle, (ii) —$C_{1-5}$ alkoxy, (iii) —OH, (iv) hydrogen, (v) C(O)—$C_{1-3}$ alkyl, or (vi) —$(CH_2)_{1-5}C(O)NR_9R_{10}$;
8) $R_8$ is (i) hydrogen, (ii) halogen, (iii) $NO_2$, (iv) —CN, (v) —$OR_{10}$, (vi) —$NHSO_2$—$C_{1-3}$alkyl, (vii) —NHCO—$C_{1-5}$ alkyl, (viii) oxime, (ix) hydrazine, (x) —$NR_9R_{10}$, (xi) $HSO_2$, (xii) $HSO_3$, (xiii) thio-$C_{1-5}$ alkyl, (xiv) $C_{1-5}$ acyloxy, (xv) $H_2PO_3$, (xvi) thiol, (xvii) —$COOR_9$, (xiii) $C_{1-5}$ alkynyl, or (xix) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy;
9) $R_9$ is hydrogen or $C_{1-3}$ alkyl; and
10) $R_{10}$ is hydrogen, or $C_{1-5}$ alkyl optionally substituted with —OH.

In a third principal embodiment the compounds of the present invention are phenylthiol, phenylamine, and multicyclic-phenolic related compounds of the following structure (III):

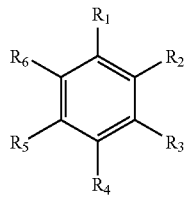

(III)

wherein:
1) $R_1$ is $(CH_2)_nSR_7$, $(CH_2)_nNHR_7$, or $OR_7$;
2) n is 0, 1, 2, or 3,
3) $R_2$, $R_3$, $R_4$, $R_5$ and $R_6$ are independently selected from (i) hydrogen, (ii) halogen, (iii) $NO_2$, (iv) —CN, (v) —$OR_{10}$, (vi) —$NHSO_2$—$C_{1-3}$alkyl, (vii) —NHCO—$C_{1-5}$ alkyl, (viii) oxime, (ix) hydrazine, (x) —$NR_9R_{10}$, (xi) $HSO_2$, (xii) $HSO_3$, (xiii) thio-$C_{1-5}$ alkyl, (xiv) $C_{1-5}$ acyloxy, (xv) $H_2PO_3$, (XVI) thiol, (xvii) —$COOR_9$, (xviii) $C_{1-5}$ alkyl, or (xix) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy;
4) alternatively, $R_3$ and $R_4$, or $R_4$ and $R_5$, combine to form a fused ring-structure which is cycloalkyl, aryl, or heterocyclic selected from phenyl, cyclopentyl, cyclohexyl, pyrrole, furan, thiophene, pyrazole, pyridine, —X—$(CH_2)_{n'}$—X— wherein n' is 1 and X is nitrogen, sulfur, or oxygen, and —$(CH)_{n''}XH$— wherein n" is 2 and X is as defined above;
5) $R_7$ is (i) substituted or unsubstituted alkyl, alkenyl, aryl, or heterocycle, (ii) —$C_{1-5}$ alkoxy, (iii) hydrogen, (iv) —$NR_9R_{10}$, (v) C(O)—$C_{1-3}$ alkyl, or (vi) —$(CH_2)_mC(O)NR_9R_{10}$;
6) $R_9$ is hydrogen or $C_{1-3}$ alkyl;
7) $R_{10}$ is hydrogen, or $C_{1-5}$ alkyl optionally substituted with —OH;
8) m is 1, 2, 3, 4, or 5; and
9) provided that when $R_1$ is $OR_7$, $R_3$ and $R_4$, or $R_4$ and $R_5$, combine to form a fused ring-structure which is cycloalkyl, aryl, or heterocyclic selected from phenyl, cyclopentyl, cyclohexyl, pyrrole, furan, thiophene, pyrazole, pyridine, —X—$(CH_2)_{n'}$—X— wherein n' is 1 and X is nitrogen, sulfur, or oxygen, and —$(CH)_{n''}XH$— wherein n" is 2 and X is as defined above.

In a fourth principal embodiment the compounds of the present invention are benzothiamide and thiophene amine derivatives defined by structures (IV) or (V):

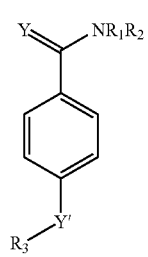

(IV)

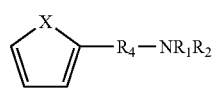

(V)

wherein:
1) $R_1$, $R_2$, and $R_3$ are independently (i) substituted or unsubstituted alkyl, alkenyl, aryl, or heterocycle, (ii) hydrogen, (iii) C(O)—$C_{1-3}$ alkyl, or (iv) —$(CH_2)_{1-5}C(O)NR_9R_{10}$;
2) $R_9$ is hydrogen or $C_{1-3}$ alkyl;
3) $R_{10}$ is hydrogen, or $C_{1-5}$ alkyl optionally substituted with —OH;
4) Y and Y' are independently oxygen or sulfur,
5) X is oxygen, sulfur, or nitrogen; and
6) $R_4$ is $C_{1-5}$ alkyl, optionally substituted by —OH, or $NR_9R_9$.

DETAILED DESCRIPTION OF THE INVENTION

Discussion

As noted above, compounds for inhibiting or preventing melanin formation in skin have been discovered for the treatment of various melanin-associated conditions. For example, the compound can be used as a "vanity" product, to lighten the skin of an individual, especially of dark skinned individuals. Alternatively, the compound can be used to reduce uneven pigmentation marks and surface color irregularities, or to diminish pigmented skin blemishes such as freckles and age spots and hyperpigmentation-related medical conditions such as melasma, ochronosis, and lentigo. The compounds can also be used to lighten hair when applied to skin containing pigmented hair follicles, and to lessen postinflammatory hyperpigmentation resulting from trauma or invasive surgery from a face lift, laser treatment, or cosmetic surgery. The active or functional compounds can also be used to reduce skin pigmentation in normal skin adjacent to areas affected by vitiligo, thereby diminishing the contrast in color between normal and vitiligo affected skin.

The invention thus provides a method for lightening mammalian skin that includes applying or otherwise administering an effective treatment amount of an active skin-lightening compound selected from a benzimidazole, a phenylthiourea, a phenylthiol, a bi- or multicyclic phenol, thiopheneamine, a benzothiamide, a phenylamine, or a pharmaceutically acceptable salt or ester thereof, optionally in a pharmaceutically acceptable carrier, to a mammalian subject in need thereof. The invention also includes a pharmaceutical composition for topical or general systemic administration, including oral, intradermal, transdermal, occlusive patch, intraveneous, and parenteral formulations, that includes an effective pigment inhibiting amount of the compound. The present invention is principally concerned with compositions that inhibit mammalian tyrosinase activity, and which thus have medicinal and/or cosmetic value. However, the present invention can also extend to compounds that inhibit melanin formation within melanocytes through mechanisms other than tyrosinase activity.

Many of the compounds also possess other activities that are beneficial when integrated into the compositions of the present invention. For example, many of the compounds also absorb UV light, and can thus be used to block the harmful effects of the sun's rays. Some of the compounds also possess antioxidant properties, and thus can inhibit oxidative damage to the skin, or contribute to the stability of the formulation.

Furthermore, although unrelated to skin pigmentation per se, some of the compounds of the present invention may also inhibit tyrosine hydroxylase (TH). This enzyme is structurally dissimilar from tryosinase, but also catalyzes the formation of DOPA from tysosine. TH is critical for the formation of catecolamines. Therefore, some of the compounds of the present invention which coincidentally inhibit TH activity may have utility in reducing catecholamine biosynthesis, for instance for use as inhibitor "probes" in laboratory experiments where reduction in catacholamine pools is desirable. [30-32]

Compounds of the Present Invention

In a first principal embodiment the compounds of the present invention are benzimidazolethiol and phenylthiourea related compounds represented by the following formula (I):

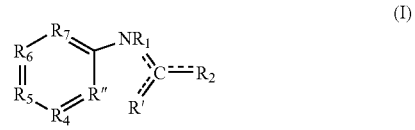

wherein:
a. $R_1$ is H or a valence for bonding;
b. $R_2$ is S, or SH;
c. one of the dotted lines ( - - - ) represents a bond;
d. $R_4$, $R_5$, $R_4$, and $R_7$ are independently $CR_8$, or N;
e. $R_8$ is (i) hydrogen, (ii) halogen, (iii) $NO_2$, (iv) —CN, (v) —$OR_{10}$, (vi) —$NHSO_2$—$C_{1-3}$alkyl, (vii) —NHCO—$C_{1-5}$ alkyl, (viii) oxime, (ix) hydrazine, (x) —$NR_9R_{10}$, (xi) $HSO_2$, (xii) $HSO_3$, (xiii) thio-$C_{1-5}$ alkyl, (xiv) $C_{1-5}$ acyloxy, (xv) $H_2PO_3$, (xvi) thiol, (xvii) —$COOR_9$, (xviii) $C_{1-5}$ alkynyl, or (xix) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy;
f. $R_9$ is hydrogen or $C_{1-3}$ alkyl;
g. $R_{10}$ is hydrogen, or $C_{1-5}$ alkyl optionally substituted with —OH;
h. R" is C or CH;
i. when R" is C:
   i. R' is $CR_8$, $C(R_8)_2$, N or NH, and forms a bond with R";
   ii. 1 or 2 of $R_5$ and $R_6$ are N or $COR_{10}$ other than COH, the remainder of $R_4$, $R_5$, $R_6$ and $R_7$ being CH; and
j. when R" is CH, R' is $CH_3$ or $NH_2$.

A first series of subembodiments of the first principal embodiment is defined when $R_1$, $R_2$, and R' are as defined above, $R_4$, $R_5$, $R_6$, and $R_7$ are independently $CR_8$, R" is CH, and:

1) $R_8$ is (i) hydrogen, (ii) halogen, (iii) $NO_2$, (iv) —CN, (v) —$OR_{10}$, (viii) —$NR_9R_{10}$, (xi) $C_{1-5}$ acyloxy, (xii) thiol, (xiii) $COOR_9$, or (xiv) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy, 2) $R_8$ is (i) hydrogen, (ii) halogen, (iii) $NO_2$, (iv) CN, (v) —$OR_9$, (viii) —$NR_9R_9$, (xi) $C_{1-3}$ acyloxy, (xii) thiol, (xiii) $COOR_9$, or (xiv) —$C_{1-3}$ alkyl, —$C_{1-3}$ alkenyl, aryl, heteroaryl, or heterocycle, optionally substituted with one or more of —OH, —SH, C(O)H, $COOR_9$, $C_{1-5}$ acyloxy, halogen, $NR_9R_9$, $C_{1-3}$ thioether, or $C_{1-3}$ alkoxy, 3) $R_8$ is (i) hydrogen, (ii) halogen, (v) $OR_9$, (viii) —$N_9R_9$, (xii) thiol, or (xiv) —$C_{1-3}$ alkyl or alkenyl optionally substituted with one or more of —OH, —SH, halogen, or $NH_2$;

4) $R_8$ is $C_{1-3}$ alkyl;

5) $R_8$ is $OR_{10}$ or $OR_9$; or

6) $R_4$, $R_5$, $R_6$, and $R_7$ are independently selected from CH, C(OH), C(SH), $CNH_2$, $C(CH_3)$, $C(OCH_3)$, CF, $C(CF_3)$, and C(CHCHBr).

A second series of subembodiments of the first principal embodiment is defined when $R_1$, $R_2$, and R' are as defined above, R" is CH, and:

1) $R_4$, $R_5$, $R_6$, and $R_7$ are independently selected from $CR_8$, 2 or 3 of $R_4$, $R_5$, $R_6$, and $R_7$ are CH, and $R_8$ is (i) hydrogen, (ii) halogen, (iii) $NO_2$, (iv) —CN, (v) —$OR_{10}$, (vi) —$NR_9R_{10}$, (vii) $C_{1-5}$ acyloxy, (viii) thiol, (ix) $COOR_9$, or (x) —$C_{1-5}$ alkyl, —$C_{1-5}$ alkenyl, aryl, heteroaryl, or heterocycle, optionally substituted with one or more of —OH, —SH, C(O)H, COOR$_9$, C$_{1-5}$ acyloxy, halogen, NR$_9$R$_{10}$, C$_{1-5}$ thioether, or C$_{1-5}$ alkoxy, 2) R$_4$, R$_5$, R$_6$, and R$_7$ are independently selected from CR$_8$, 2 or 3 of R$_4$, R$_5$, R$_6$, and R$_7$ are CH, and R$_8$ is (i) hydrogen, (ii) halogen, (iii) —OR$_9$, (iv) —OH, (v) —NR$_9$R$_9$, (vi) thiol, or (vii) —C$_{1-3}$ alkyl or alkenyl optionally substituted with one or more of —OH, —SH, halogen, or NH$_2$;

3) R$_4$, R$_5$, R$_6$, and R$_7$ are independently selected from CR$_8$, 2 or 3 of R$_4$, R$_5$, R$_6$, and R$_7$ are CH, and R$_8$ is C$_{1-3}$ alkyl;

4) R$_4$, R$_5$, R$_6$, and R$_7$ are independently selected from CR$_8$, R$_8$ is OR$_9$, and 2 or 3 of R$_4$, R$_5$, R$_6$, and R$_7$ are CH; or 5) R$_4$, R$_5$, R$_6$, and R$_7$ are independently selected from CH, C(OH), C(SH), CNH$_2$, C(CH$_3$), C(OCH$_3$), CF, C(CF$_3$), and C(CHCHBr), and 2 or 3 of R$_4$, R$_5$, R$_6$, and R$_7$ are CH.

A third series of subembodiments of the first principal embodiment is defined when R$_1$ and R$_2$ are as defined above, R" is CH, and:

1) R$_4$, R$_5$, R$_6$, and R$_7$ are independently selected from CR$_8$, and R' is NH$_2$;

2) R$_4$, R$_5$, R$_6$, and R$_7$ are independently selected from CR$_8$, R$_8$ is (i) hydrogen, (ii) halogen, (iii) NO$_2$, (iv) —CN, (v) —OR$_{10}$, (viii) —NR$_9$R$_{10}$, (xi) C$_{1-5}$ acyloxy, (xii) thiol, (xiii) COOR$_9$, or (xiv) —C$_{1-5}$ alkyl, —C$_{1-5}$ alkenyl, aryl, heteroaryl, or heterocycle, optionally substituted with one or more of —OH, —SH, C(O)H, COOR$_9$, C$_{1-5}$ acyloxy, halogen, NR$_9$R$_{10}$, C$_{1-5}$ thioether, or C$_{1-5}$ alkoxy, 2 or 3 of R$_4$, R$_5$, R$_6$ and R$_7$ are CH, and R' is NH$_2$;

3) R$_4$, R$_5$, R$_6$, and R$_7$ are independently selected from CR$_8$, R$_8$ is (i) hydrogen, (ii) halogen, (v) —OR$_9$, (vii) —OH, (viii) —NR$_9$R$_9$, (xii) thiol, or (xiv) —C$_{1-3}$ alkyl or alkenyl optionally substituted with one or more of —OH, —SH, halogen, or NH$_2$, 2 or 3 of R$_4$, R$_5$, R$_6$, and R$_7$ are CH, and R' is NH$_2$;

4) R$_4$, R$_5$, R$_6$, and R$_7$ are independently selected from CR$_8$, R$_8$ is C$_{1-3}$ alkyl, OR$_{10}$, or OR$_9$, 2 or 3 of R$_4$, R$_5$, R$_6$, and R$_7$ are CH, and R' is NH$_2$;

5) R$_4$, R$_5$, R$_6$, and R$_7$ are independently selected from CH, C(OH), C(SH), CNH$_2$, C(CH$_3$), C(OCH$_3$), CF, CCF$_3$, and C(CHCHPBr), 2 or 3 of R$_4$, R$_5$, R$_6$, and R$_7$ are CH; and R' is NH$_2$;

6) R$_4$, R$_5$, R$_6$, and R$_7$ are independently selected from CR$_8$, and R' is CH$_3$;

7) R$_4$, R$_5$, R$_6$, and R$_7$ are independently selected from CR$_8$, R$_8$ is (i) hydrogen, (ii) halogen, (iii) NO$_2$, (iv) —CN, (v) —OR$_{10}$, (viii) —NR$_9$R$_{10}$, (xi) C$_{1-5}$ acyloxy, (xii) thiol, (xiii) COOR$_9$, or (xiv) —C$_{1-5}$ alkyl, —C$_{1-5}$ alkenyl, aryl, heteroaryl, or heterocycle, optionally substituted with one or more of —OH, —SH, C(O)H, COOR$_9$, C$_{1-5}$ acyloxy, halogen, NR$_9$R$_{10}$, C$_{1-5}$ thioether, or C$_{1-5}$ alkoxy, 2 or 3 of R$_4$, R$_5$, R$_6$, and R$_7$ are CH, and R' is CH$_3$;

8) R$_4$, R$_5$, R$_6$, and R$_7$ are independently selected from CR$_8$, R$_8$ is (i) hydrogen, (ii) halogen, (v) —OR$_9$, (vii) —OH, (viii) —NR$_9$R$_9$, (xii) thiol, or (xiv) —C$_{1-3}$ alkyl or alkenyl optionally substituted with one or more of —OH, —SH, halogen, or NH$_2$, 2 or 3 of R$_4$, R$_5$, R$_6$, and R$_7$ are CH, and R' is CH$_3$;

9) R$_4$, R$_5$, R$_6$, and R$_7$ are independently selected from C$_8$, R$_8$ is R$_8$ is C$_{1-3}$ alkyl or OR$_9$, 2 or 3 of R$_4$, R$_5$, R$_6$, and R$_7$ are CH, and R' is CH$_3$;

10) R$_4$, R$_5$, R$_6$, and R$_7$ are independently selected from CH, C(OH), C(SH), CNH$_2$, C(CH$_3$), C(OCH$_3$), CF, CCF$_3$, and C(CHCHBr), 2 or 3 of R$_4$, R$_5$, R$_6$, and R$_7$ are CH, and R' is CH$_3$;

A fourth series of subembodiments of the first principal embodiment is defined when R$_1$ and R$_2$ are as defined above, R" is C, R' is N or NH, and:

1) 1 or 2 of R$_5$ and R$_6$ are COR$_{10}$ other than COH, the remainder of R$_4$, R$_5$, R$_6$, and R$_7$ being CH;

2) 1 or 2 of R$_5$ and R$_6$ are COR$_9$ other than COH, the remainder of R$_4$, R$_5$, R$_6$, and R$_7$ being CH;

3) 1 or 2 of R$_5$ and R$_6$ are N, the remainder of R$_4$, R$_5$, R$_6$, and R$_7$ being CH;

4) R$_5$ is COR$_9$ other than COH, and R$_4$, R$_6$, and R$_7$ are CH;

5) R$_6$ is COR$_9$ other than COH, and R$_4$, R$_5$, and R$_7$ are CH; or

6) R$_5$ and R$_6$ are COR$_9$ other than COH, and R$_4$ and R$_7$ are CH.

A fifth series of subembodiments of the first principal embodiment are defined when R$_1$ and R$_2$ are as defined above, R" is C, R' is CH or CH$_2$, and:

1) 1 or 2 of R$_5$ and R$_6$ are COR$_{10}$ other than COH, the remainder of R$_4$, R$_5$, R$_6$, and R$_7$ being CH;

2) 1 or 2 of R$_5$ and R$_6$ are COR$_9$ other than COH, the remainder of R$_4$, R$_5$, R$_6$, and R$_7$ being CH;

3) 1 or 2 of R$_5$ and R$_6$ are N, the remainder of R$_4$, R$_5$, R$_6$, and R$_7$ being CH;

4) R$_5$ is COR$_9$ other than COH, and R$_4$, R$_6$, and R$_7$ are CH;

5) R$_6$ is COR$_9$ other than COH, and R$_4$, R$_5$, and R$_7$ are CH; or

6) R$_5$ and R$_6$ are COR$_9$ other than COH, and R$_4$ and R$_7$ are CH.

A first series of preferred species of the first principal embodiment are defined when R$_1$ and R$_2$ are as defined above, R" is C, R' is NH or N, and:

1) R$_5$ is COCH$_3$, and R$_4$, R$_6$, and R$_7$ are CH;

2) R$_6$ is COCH$_3$, and R$_4$, R$_5$, and R$_7$ are CH;

3) R$_5$ and R$_6$ are COCH$_3$, and R$_4$ and R$_7$ are CH;

A second series of preferred species of the first principal embodiment are defined when R$_1$ and R$_2$ are as defined above, R" is CH, R' is NH$_2$, and:

1) R$_4$, R$_5$, R$_6$, and R$_7$ are CH;

2) R$_4$ is CCH$_3$, and R$_5$, R$_6$, and R$_7$ are CH;

3) R$_5$ is CCH$_3$, and R$_4$, R$_6$, and R$_7$ are CH;

4) R$_6$ is CCH$_3$, and R$_4$, R$_5$, and R$_7$ are CH;

5) R$_7$ is CCH$_3$, and R$_4$, R$_5$, and R$_6$ are CH;

6) R$_4$ is COCH$_3$, and R$_5$, R$_6$, and R$_7$ are CH;

7) R$_5$ is COCH$_3$, and R$_4$, R$_6$, and R$_7$ are CH;

8) R$_6$ is COCH$_3$, and R$_4$, R$_5$, and R$_7$ are CH;

9) R$_7$ is COCH$_3$, and R$_4$, R$_5$, and R$_6$ are CH;

10) R$_4$ is CF, and R$_5$, R$_6$, and R$_7$ are CH;

11) R$_5$ is CF, and R$_4$, R$_6$, and R$_7$ are CH;

12) R$_6$ is CF, and R$_4$, R$_5$, and R$_7$ are CH;

13) R$_7$ is CF, and R$_4$, R$_5$, and R$_6$ are CH;

14) R$_4$ is COH, and R$_5$, R$_6$, and R$_7$ are CH;

15) R$_5$ is COH, and R$_4$, R$_6$, and R$_7$ are CH;

16) R$_6$ is COH, and R$_4$, R$_5$, and R$_7$ are CH;

17) R$_7$ is COH, and R$_4$, R$_5$, and R$_6$ are CH;

18) 2 of R$_4$, R$_5$, R$_6$ are R$_7$ are CCH$_3$, and 2 of R$_4$, R$_5$, R$_6$, and R$_7$ are CH;

19) 2 of R$_4$, R$_5$, R$_6$ are R$_7$ are COCH$_3$, and 2 of R$_4$, R$_5$, R$_6$, and R$_7$ are CH;

20) 2 of R$_4$, R$_5$, R$_6$ are R$_7$ are CF, and 2 of R$_4$, R$_5$, R$_6$, and R$_7$ are CH; or 21) 2 of R$_4$, R$_5$, R$_6$ are R$_7$ are COH, and 2 of R$_4$, R$_5$, R$_6$, and R$_7$ are CH;

A third series of preferred species of the first principal embodiment are defined when R" is CH, R' is CH$_3$, and R$_4$, R$_5$, R$_6$, and R$_7$ are as defined in any one of the second series of preferred species.

In a second principal embodiment the compounds of the present invention are benzimidazoles and phenylthiourea related compounds represented by the following formula (II):

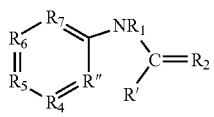

(II)

wherein:
1) $R_1$ is H;
2) $R_2$ is selenium;
3) R" is C or CH;
4) when R" is C, R' is $C(R_8)_2$ or $NR_3$, and forms a bond with R";
5) when R" is CH, R' is $CH_3$ or $NH_2$;
6) $R_4$, $R_5$, $R_6$, and $R_7$ are independently $CR_8$, or N;
7) $R_3$ is (i) substituted or unsubstituted alkyl, alkenyl, aryl, or heterocycle, (ii) —$C_{1-5}$ alkoxy, (iii) —OH, (iv) hydrogen, (v) C(O)—$C_{1-3}$ alkyl, or (vi) —$(CH_2)_{1-5}C(O)NR_9R_{10}$;
8) $R_8$ is (i) hydrogen, (ii) halogen, (iii) $NO_2$, (iv) —CN, (v) —$OR_{10}$, (vi) —$NHSO_2$—$C_{1-3}$alkyl, (vii) —NHCO—$C_{1-5}$ alkyl, (viii) oxime, (ix) hydrazine, (x) —$NR_9R_{10}$, (xi) $HSO_2$, (xii) $HSO_3$, (xiii) thio-$C_{1-5}$ alkyl, (xiv) $C_{1-5}$ acyloxy, (xv) $H_2PO_3$, (xvi) thiol, (xvii) —$COOR_9$, (xviii) $C_{1-5}$ alkynyl, or (xix) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy;
9) $R_9$ is hydrogen or $C_{1-3}$ alkyl; and
10) $R_{10}$ is hydrogen, or $C_{1-5}$ alkyl optionally substituted with —OH.

A first series of subembodiments of the second principal embodiment are defined when $R_1$, $R_2$, R' and R" are as defined above, $R_4$, $R_5$, $R_6$ and $R_7$ are $CR_8$, and:
1) $R_8$ is (i) hydrogen, (ii) halogen, (iii) $NO_2$, (iv) —CN, (v) —$OR_{10}$, (viii) —$NR_9R_{10}$, (xi) $C_{1-5}$ acyloxy, (xii) thiol, (xiii) $COOR_9$, or (xiv) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy;
2) $R_8$ is (i) hydrogen, (ii) halogen, (iii) $NO_2$, (iv) —CN, (v) —$OR_9$, (viii) —$NR_9R_9$, (xi) $C_{1-3}$ acyloxy, (xii) thiol, (xiii) $COOR_9$, or (xiv) —$C_{1-3}$ alkyl, —$C_{1-3}$ alkenyl, aryl, heteroaryl, or heterocycle, optionally substituted with one or more of —OH, —SH, C(O)H, $COOR_9$, $C_{1-5}$ acyloxy, halogen, $NR_9R_9$, $C_{1-3}$ thioether, or $C_{1-3}$ alkoxy;
3) $R_8$ is (i) hydrogen, (ii) halogen, (v) —$OR_9$, (viii) —$NR_9R_9$, (xii) thiol, or (xiv) —$C_{1-3}$ alkyl or alkenyl optionally substituted with one or more of —OH, —SH, halogen, or $NH_2$;
4) $R_8$ is $C_{1-3}$ alkyl;
5) $R_8$ is $OR_{10}$ or $OR_9$; or
6) $R_4$, $R_5$, $R_6$, and $R_7$ are independently selected from CH, C(OH), C(SH), $CNH_2$, $C(CH_3)$, $C(OCH_3)$, CF, $CCF_3$, and C(CHCHBr).

A second series of subembodiments of the second principal embodiment is defined when $R_1$, $R_2$, R' and R" are as defined above, and:
1) $R_4$, $R_5$, $R_6$, and $R_7$ are independently selected from $CR_8$, 2 or 3 of $R_4$, $R_5$, $R_6$, and $R_7$ are CH, and $R_8$ is (i) hydrogen, (ii) halogen, (iii) $NO_2$, (iv) —CN, (v) —$OR_{10}$, (vi) —$NR_9R_{10}$, (vii) $C_{1-5}$ acyloxy, (viii) thiol, (ix) $COOR_9$, or (x) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy,
2) $R_4$, $R_5$, $R_6$, and $R_7$ are independently selected from $CR_8$, 2 or 3 of $R_4$, $R_5$, $R_6$, and $R_7$ are CH, and $R_8$ is (i) hydrogen, (ii) halogen, (iii) —$OR_9$, (iv) —OH, (v) —$NR_9R_9$, (vi) thiol, or (vii) —$C_{1-3}$ alkyl or alkenyl optionally substituted with one or more of —OH, —SH, halogen, or $NH_2$;
3) $R_4$, $R_5$, $R_6$, and $R_7$ are independently selected from $CR_8$, 2 or 3 of $R_4$, $R_5$, $R_6$, and $R_7$ are CH, and $R_8$ is $C_{1-3}$ alkyl;
4) $R_4$, $R_5$, $R_6$, and $R_7$ are independently selected from $CR_8$, $R_8$ is $OR_9$, and 2 or 3 of $R_4$, $R_5$, $R_6$, and $R_7$ are CH; and
5) $R_4$, $R_5$, $R_6$, and $R_7$ are independently selected from CH, C(OH), C(SH), $CNH_2$, $C(CH_3)$, $C(OCH_3)$, CF, $CCF_3$, and C(CHCHBr), and 2 or 3 of $R_4$, $R_5$, $R_6$, and $R_7$ are CH.

A third series of subembodiments of the second principal embodiment are defined when $R_1$ and $R_2$ are as defined above, R" is C, and:
1) $R_4$, $R_5$, $R_6$, and $R_7$ are independently selected from $CR_8$, and R' is $NR_3$;
2) $R_4$, $R_5$, $R_6$, and $R_7$ are independently selected from $CR_8$, $R_8$ is (i) hydrogen, (ii) halogen, (iii) $NO_2$, (iv) —CN, (v) —$OR_{10}$, (viii) —$NR_9R_{10}$, (xi) $C_{1-5}$ acyloxy, (xii) thiol, (xiii) $COOR_9$, or (xiv) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy, 2 or 3 of $R_4$, $R_5$, $R_6$ and $R_7$ are CH, and R' is $NR_3$;
3) $R_4$, $R_5$, $R_6$, and $R_7$ are independently selected from $CR_8$, $R_8$ is (i) hydrogen, (ii) halogen, (v) —$R_9$, (vii) —OH, (viii) —$NR_9R_9$, (xii) thiol, or (xiv) —$C_{1-3}$ alkyl or alkenyl optionally substituted with one or more of —OH, —SH, halogen, or $NH_2$, 2 or 3 of $R_4$, $R_5$, $R_6$, and $R_7$ are CH, and R' is $NR_3$;
4) $R_4$, $R_5$, $R_6$, and $R_7$ are independently selected from $CR_8$, $R_8$ is $R_8$ is $C_{1-3}$ alkyl or $OR_9$, 2 or 3 of $R_4$, $R_5$, $R_6$, and $R_7$ are CH, and R' is $NR_3$;
5) $R_4$, $R_5$, $R_6$, and $R_7$ are independently selected from CH, C(OH), C(SH), $CNH_2$, $C(CH_3)$, $C(OCH_3)$, CF, $CCF_3$, and C(CHCHBr), 2 or 3 of $R_4$, $R_5$, and $R_7$ are CH; and R' is $NR_3$;
6) $R_4$, $R_5$, $R_6$, and $R_7$ are independently selected from $CR_8$, R' is $NR_3$, and $R_3$ is hydrogen, or $C_{1-5}$ alkyl optionally substituted with —OH;
7) $R_4$, $R_5$, $R_6$, and $R_7$ are independently selected from $CR_8$, $R_8$ is (i) hydrogen, (ii) halogen, (iii) $NO_2$, (iv) —CN, (v) —$OR_{10}$, (viii) —$NR_9R_{10}$, (xi) $C_{1-5}$ acyloxy, (xii) thiol, (xiii) $COOR_9$, or (xiv) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy, 2 or 3 of $R_4$, $R_5$, $R_6$, and $R_7$ are CH, R' is $NR_3$, and $R_3$ is hydrogen, or $C_{1-5}$ alkyl optionally substituted with —OH;
8) $R_4$, $R_5$, $R_6$, and $R_7$ are independently selected from $CR_8$, $R_8$ is (i) hydrogen, (ii) halogen, (v) —$OR_9$, (vii) —OH, (viii) —$NR_9R_9$, (xii) thiol, or (xiv) —$C_{1-3}$ alkyl or alkenyl optionally substituted with one or more of —OH, —SH, halogen, or $NH_2$, 2 or 3 of $R_4$, $R_5$, $R_6$, and $R_7$ are CH, R' is $NR_3$, and $R_3$ is hydrogen, or $C_{1-5}$ alkyl optionally substituted with —OH;
9) $R_4$, $R_5$, $R_6$, and $R_7$ are independently selected from $CR_8$, $R_8$ is $R_8$ is $C_{1-3}$ alkyl or $OR_9$, 2 or 3 of $R_4$, $R_5$, $R_6$, and $R_7$ are CH, R' is $NR_3$, and $R_3$ is hydrogen, or $C_{1-5}$ alkyl optionally substituted with —OH;
10) $R_4$, $R_5$, $R_6$, and $R_7$ are independently selected from CH, C(OH), C(SH), $CNH_2$, $C(CH_3)$, $C(OCH_3)$, CF, $CCF_3$, and C(CHCHBr), 2 or 3 of $R_4$, $R_5$, $R_6$, and $R_7$ are CH; R' is $NR_3$; and $R_3$ is hydrogen, or $C_{1-5}$ alkyl optionally substituted with —OH;

11) $R_4$, $R_5$, $R_6$, and $R_7$ are independently selected from $CR_8$, R' is $NR_3$, and $R_3$ is hydrogen or $C_{1-3}$ alkyl;
12) $R_4$, $R_5$, $R_6$, and $R_7$ are independently selected from $CR_8$, $R_8$ is (i) hydrogen, (ii) halogen, (iii) $NO_2$, (iv) —CN, (v) —$OR_{10}$, (viii) —$NR_9R_{10}$, (xi) $C_{1-5}$ acyloxy, (xii) thiol (xiii) $COOR_9$, or (xiv) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy, 2 or 3 of $R_4$, $R_5$, $R_6$, and $R_7$ are CH, R' is $NR_3$, and $R_3$ is hydrogen or $C_{1-3}$ alkyl;
13) $R_4$, $R_5$, $R_6$, and $R_7$ are independently selected from $CR_8$, $R_8$ is (i) hydrogen, (ii) halogen, (v) —$OR_9$, (vii) —OH, (viii) —$NR_9R_9$, (xii) thiol or (xiv) —$C_{1-3}$ alkyl or alkenyl optionally substituted with one or more of —OH, —SH, halogen, or $NH_2$, 2 or 3 of $R_4$, $R_5$, $R_6$, and $R_7$ are CH, R' is $NR_3$, and $R_3$ is hydrogen or $C_{1-3}$ alkyl;
14) $R_4$, $R_5$, $R_6$, and $R_7$ are independently selected from $CR_8$, $R_8$ is $R_8$ is $C_{1-3}$ alkyl or $OR_9$, 2 or 3 of $R_4$, $R_5$, $R_6$, and $R_7$ are CH, R' is $NR_3$, and $R_3$ is hydrogen or $C_{1-3}$ alkyl; or
15) $R_4$, $R_5$, $R_6$, and $R_7$ are independently selected from CH, C(OH), C(SH), $CNH_2$, $C(CH_3)$, $C(OCH_3)$, CF, $CCF_3$, and C(CHCHBr), 2 or 3 of $R_4$, $R_5$, $R_6$, and $R_7$ are CH; R' is $NR_3$, and $R_3$ is hydrogen or $C_{1-3}$ alkyl.

A fourth series of subembodiments of the second principal embodiment is defined when $R_1$ and $R_2$ are as defined above, R'' is CH, and:
1) $R_4$, $R_5$, $R_6$, and $R_7$ are independently selected from $CR_8$, and R' is $NH_2$;
2) $R_4$, $R_5$, $R_6$, and $R_7$ are independently selected from $CR_8$, $R_8$ is (i) hydrogen, (ii) halogen, (iii) $NO_2$, (iv) (N, (v) —$OR_{10}$, (viii) —$NR_9R_{10}$, (xi) $C_{1-5}$ acyloxy, (xii) thiol, (xiii) $COOR_9$, or (xiv) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy, 2 or 3 of $R_4$, $R_5$, $R_6$, and $R_7$ are CH, and R' is $NH_2$;
3) $R_4$, $R_5$, $R_6$, and $R_7$ are independently selected from $CR_8$, $R_8$ is (i) hydrogen, (ii) halogen, (v) —$OR_9$, (vii) —OH, (viii) —$NR_9R_9$, (xii) thiol, or (xiv) —$C_{1-3}$ alkyl or alkenyl optionally substituted with one or more of —OH, —SH, halogen, or $NH_2$, 2 or 3 of $R_4$, $R_5$, $R_6$, and $R_7$ are CH, and R' is $NH_2$;
4) $R_4$, $R_5$, $R_6$, and $R_7$ are independently selected from $CR_8$, $R_8$ is $R_8$ is $C_{1-3}$ alkyl or $OR_9$, 2 or 3 of $R_4$, $R_5$, $R_6$, and $R_7$ are CH, and R' is $NH_2$;
5) $R_4$, $R_5$, $R_6$, and $R_7$ are independently selected from CH, C(OH), C(SH), $CNH_2$, $C(CH_3)$, $C(OCH_3)$, CF, $CCF_3$, and C(CHCHBr), 2 or 3 of $R_4$, $R_5$, $R_6$, and $R_7$ are CH; and R' is $NH_2$;
6) $R_4$, $R_5$, $R_6$, and $R_7$ are independently selected from $CR_8$, and R' is $CH_3$;
7) $R_4$, $R_5$, $R_6$, and $R_7$ are independently selected from $CR_8$, $R_8$ is (i) hydrogen, (ii) halogen, (iii) $NO_2$, (iv) —CN, (v) —$OR_{10}$, (viii) —$NR_9R_{10}$, (xi) $C_{1-5}$ acyloxy, (xii) thiol, (xiii) $COOR_9$, or (xiv) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy, 2 or 3 of $R_4$, $R_5$, $R_6$, and $R_7$ are CH, R' is $NR_3$, and R' is $CH_3$;
8) $R_4$, $R_5$, $R_6$, and $R_7$ are independently selected from $CR_8$, $R_8$ is (i) hydrogen, (ii) halogen, (v) —$OR_9$, (vii) —OH, (viii) —$NR_9R_9$, (xii) thiol, or (xiv) —$C_{1-3}$ alkyl or alkenyl optionally substituted with one or more of —OH, —SH, halogen, or $NH_2$, 2 or 3 of $R_4$, $R_5$, $R_6$, and $R_7$ are CH, and R' is $CH_3$;
9) $R_4$, $R_5$, $R_6$, and $R_7$ are independently selected from $C_8$, $R_8$ is $R_8$ is $C_{1-3}$ alkyl or $OR_9$, 2 or 3 of $R_4$, $R_5$, $R_6$, and $R_7$ are CH, and R' is $CH_3$; and
10) $R_4$, $R_5$, $R_6$, and $R_7$ are independently selected from CH, C(OH), C(SH), $CNH_2$, $C(CH_3)$, $C(OCH_3)$, CF, $CCF_3$, and C(CHCHBr), 2 or 3 of $R_4$, $R_5$, $R_6$, and $R_7$ are CH; and R' is $CH_3$.

A first series of preferred species of the second principal embodiment are defined when $R_1$ and $R_2$ are as defined above, R'' is C, R' is NH, and:
1) $R_4$, $R_5$, $R_6$, and $R_7$ are CH;
2) $R_4$ is $CCH_3$, and $R_5$, $R_6$, and $R_7$ are CH;
3) $R_5$ is $CCH_3$, and $R_4$, $R_6$, and $R_7$ are CH;
4) $R_6$ is $CCH_3$, and $R_4$, $R_5$, and $R_7$ are CH;
5) $R_7$ is $CCH_3$, and $R_4$, $R_5$, and $R_6$ are CH;
6) $R_4$ is $COCH_3$, and $R_5$, $R_6$, and $R_7$ are CH;
7) $R_5$ is $COCH_3$, and $R_4$, $R_6$, and $R_7$ are CH;
8) $R_6$ is $COCH_3$, and $R_4$, $R_5$, and $R_7$ are CH;
9) $R_7$ is $COCH_3$, and $R_4$, $R_5$, and $R_6$ are CH;
10) $R_4$ is CF, and $R_5$, $R_6$, and $R_7$ are CH;
11) $R_5$ is CF, and $R_4$, $R_6$, and $R_7$ are CH;
12) $R_6$ is CF, and $R_4$, $R_5$, and $R_7$ are CH;
13) $R_7$ is CF, and $R_4$, $R_5$, and $R_6$ are CH;
14) $R_4$ is COH, and $R_5$, $R_6$, and $R_7$ are CH;
15) $R_5$ is COH, and $R_4$, $R_6$, and $R_7$ are CH;
16) $R_6$ is COH, and $R_4$, $R_5$, and $R_7$ are CH;
17) $R_7$ is COH, and $R_4$, $R_5$, and $R_6$ are CH;
18) 2 of $R_4$, $R_5$, $R_6$ are $R_7$ are $CCH_3$, and 2 of $R_4$, $R_5$, $R_6$, and $R_7$ are CH;
19) 2 of $R_4$, $R_5$, $R_6$ are $R_7$ are $COCH_3$, and 2 of $R_4$, $R_5$, $R_6$, and $R_7$ are CH;
20) 2 of $R_4$, $R_5$, $R_6$ are $R_7$ are CF, and 2 of $R_4$, $R_5$, $R_6$, and $R_7$ are CH; or
21) 2 of $R_4$, $R_5$, are $R_7$ are COH, and 2 of $R_4$, $R_5$, $R_6$, and $R_7$ are CH;

A second series of preferred species of the second principal embodiment are defined when R'' is CH, R' is $NH_2$, and $R_4$, $R_5$, $R_6$, and $R_7$ are as defined in any one of the first series of preferred species.

A third series of preferred species of the present invention are defined when R'' is CH, R' is $CH_3$, and $R_4$, $R_5$, $R_6$, and $R_7$ are as defined in any one of the first series of preferred species.

In a third principal embodiment the compounds of the present invention are phenylthiol, phenylamine, and multicyclic-phenolic related compounds of the following structure (III):

(III)

wherein:
1) $R_1$ is $(CH_2)_nSR_7$, $(CH_2)_nNR_7$, or $OR_7$;
2) n is 0, 1, 2, or 3,
3) $R_2$, $R_3$, $R_4$, $R_5$ and $R_6$ are independently selected from (i) hydrogen, (ii) halogen, (iii) $NO_2$, (iv) —CN, (v) —$OR_{10}$, (vi) —$NHSO_2$—$C_{1-3}$alkyl, (vii) —NHCO—$C_{1-5}$ alkyl, (viii) oxine, (ix) hydrazine, (x) —$NR_9R_{10}$, (xi) $HSO_2$, (xii) $HSO_3$, (xiii) thio-$C_{1-5}$ alkyl, (xiv) $C_{1-5}$ acyloxy, (xv) $H_2PO_3$, (xvi) thiol, (xvii) —$COOR_9$, (xviii) $C_{1-5}$ alkynyl, or (xix) —$C_{1-5}$ alkyl, —$C_{1-5}$ alkenyl, aryl, heteroaryl, or heterocycle, optionally substituted with one or more of —OH, —SH, C(O)H, COOR$_9$, $C_{1-5}$ acyloxy, halogen, NR$_9$R$_{10}$, $C_{1-5}$ thioether, or $C_{1-5}$ alkoxy, 4) alternatively, R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, pyridine, —X—(CH$_2$)$_{n'}$—X— wherein n' is 1 and X is nitrogen, sulfur, or oxygen, and —(CH)$_{n''}$—XH— wherein n" is 2 and X is as defined above;

5) R$_7$ is (i) substituted or unsubstituted alkyl, alkenyl, aryl, or heterocycle, (ii) —$C_{1-5}$ alkoxy, (iii) hydrogen, (iv) C(O)—$C_{1-3}$ alkyl, or (v) —(CH$_2$)$_m$C(O)NR$_9$R$_{10}$;

6) R$_9$ is hydrogen or $C_{1-3}$ alkyl;

7) R$_{10}$ is hydrogen, or $C_{1-5}$ alkyl optionally substituted with —OH;

8) m is 1, 2, 3, 4, or 5; and 9) provided that when R$_1$ is OR$_7$, R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, pyridine, —X—(CH$_2$)$_n$—X— wherein n' is 1 and X is nitrogen, sulfur, or oxygen, and —(CH)$_{n''}$XH— wherein n" is 2 and X is as defined above.

A first series of subembodiments of the third principal embodiment are defined when R$_1$ is (CH$_2$)SR$_7$, n is 0, 1, 2, or 3 but preferably 0, and:

1) R$_2$, R$_3$, R$_4$, R$_5$ and R$_6$ are as defined above, and R$_7$ is hydrogen, $C_{1-5}$ alkyl optionally substituted with —OH, or C(O)$C_{1-3}$ alkyl;

2) R$_2$, R$_3$, R$_4$, R$_5$ and R$_6$ are as defined above, and R$_7$ is hydrogen, $C_{1-3}$ alkyl, or C(O)$C_{1-3}$ alkyl;

3) R$_2$, R$_3$, R$_4$, R$_5$ and R$_6$ are as defined above, and R$_7$ is hydrogen;

4) R$_2$, R$_3$, R$_4$, R$_5$ and R$_6$ are independently selected from (i) hydrogen, (ii) halogen, (iii) NO$_2$, (iv) —CN, (v) —OR$_{10}$, (viii) —NR$_9$R$_{10}$, (xi) $C_{1-5}$ acyloxy, (xii) thiol, (xiii) COOR$_9$, or (xiv) —$C_{1-5}$ alkyl, —$C_{1-5}$ alkenyl, aryl, heteroaryl, or heterocycle, optionally substituted with one or more of —OH, —SH, C(O)H, COOR$_9$, $C_{1-5}$ acyloxy, halogen, NR$_9$R$_9$, $C_{1-5}$ thioether, or $C_{1-5}$ alkoxy, or (xv) —NHCO—$C_{1-5}$ alkyl; and R$_7$ is as defined above;

5) R$_2$, R$_3$, R$_4$, R$_5$ and R$_6$ are independently selected from (i) hydrogen, (ii) halogen, (iii) NO$_2$, (iv) —CN, (v) —OR$_9$, (viii) —NR$_9$R$_9$, (xi) $C_{1-3}$ acyloxy, (xii) thiol, (xiii) COOR$_9$, (xiv) —$C_{1-3}$ alkyl, —$C_{1-3}$ alkenyl, aryl, heteroaryl, or heterocycle, optionally substituted with one or more of —OH, —SH, C(O)H, COOR$_9$, $C_{1-5}$ acyloxy, halogen, NR$_9$R$_9$, $C_{1-3}$ thioether, or $C_{1-3}$ alkoxy, or (xv) —NHCO—$C_{1-3}$ alkyl; and R$_7$ is as defined above;

6) R$_2$, R$_3$, R$_4$, R$_5$ and R$_6$ are independently selected from (i) hydrogen, (ii) halogen, (v) —OR$_9$, (viii) —NR$_9$R$_9$, (xii) thiol, (xiv) —$C_{1-3}$ alkyl or alkenyl optionally substituted with one or more of —OH, —SH, halogen, or NH$_2$, or (xv) —NHCO—$C_{1-3}$ alkyl; and R$_7$ is as defined above;

7) R$_2$, R$_3$, R$_4$, R$_5$ and R$_6$ are independently selected from $C_{1-3}$ alkyl, OR$_9$, or —NHCO—CH$_3$ aryl; and R$_7$ is as defined above;

8) (a) R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, pyridine, —X—(CH$_2$)$_{n'}$—X— wherein n' is 1 and X is nitrogen, sulfur, or oxygen, and —(CH)$_{n''}$XH— wherein n" is 2 and X is as defined above; and (b) the remainder of R$_2$, R$_3$, R$_5$ and R$_6$ are independently selected from (i) hydrogen, (ii) halogen, (iii) NO$_2$, (iv) —CN, (v) —OR$_{10}$, (vi —NR$_9$R$_{10}$, (vii) $C_{1-5}$ acyloxy, (viii) thiol, (ix) COOR$_9$, or (x) —$C_{1-5}$ alkyl, —$C_{1-5}$ alkenyl, aryl, heteroaryl, or heterocycle, optionally substituted with one or more of —OH, —SH, C(O)H, COOR$_9$, $C_{1-5}$ acyloxy, halogen, NR$_9$R$_{10}$, $C_{1-5}$ thioether, or $C_{1-5}$ alkoxy; and R$_7$ is as defined above;

9) (a) R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, pyridine, —X—(CH$_2$)$_{n'}$—X— wherein n' is 1 and X is nitrogen, sulfur, or oxygen, and —CH)$_{n''}$XH— wherein n" is 2 and X is as defined above; and (b) the remainder of R$_2$, R$_3$, R$_5$ and R$_6$ are independently selected from (i) hydrogen, (ii) halogen, (iii) NO$_2$, (iv) —CN, (v) —OR$_9$, (vi) —NR$_9$R$_9$, (vii) $C_{1-3}$ acyloxy, (viii) thiol, (ix) COOR$_9$, or (x) —$C_{1-3}$ alkyl, —$C_{1-3}$ alkenyl, aryl, heteroaryl, or heterocycle, optionally substituted with one or more of —OH, —SH, C(O)H, COOR$_9$, $C_{1-5}$ acyloxy, halogen, NR$_9$R$_9$, $C_{1-3}$ thioether, or $C_{1-3}$ alkoxy, and R$_7$ is as defined above;

10) (a) R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, pyridine, —X—(CH$_2$)$_{n'}$—X— wherein n' is 1 and X is nitrogen, sulfur, or oxygen, and —(CH)$_n$—X— wherein n" is 2 and X is as defined above; and (b) the remainder of R$_2$, R$_3$, R$_5$ and R$_6$ are independently selected from (i) hydrogen, (ii) halogen, (iii) —OR$_9$, (iv) —NR$_9$R$_9$, (v) thiol, or (vi) —$C_{1-3}$ alkyl or alkenyl optionally substituted with one or more of —OH, —SH, halogen, or NH$_2$; and R$_7$ is as defined above;

11) (a) R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, pyridine, —X—(CH$_2$)$_{n'}$—X— wherein n' is 1 and X is nitrogen, sulfur, or oxygen, and —(CH)$_{n''}$XH— wherein n" is 2 and X is as defined above; and (b) the remainder of R$_2$, R$_3$, R$_5$ and R$_6$ are independently selected from $C_{1-3}$ alkyl or OR$_9$; and R$_7$ is as defined above;

12) (a) R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, and pyridine; and (b) the remainder of R$_2$, R$_3$, R$_5$ and R$_6$ are independently selected from (i) hydrogen, (ii) halogen, (iii) NO$_2$, (iv) —CN, (v) —OR$_{10}$, (vi) —NR$_9$R$_{10}$, (vii) $C_{1-5}$ acyloxy, (viii) thiol, (ix) COOR$_9$, or (x) —$C_{1-5}$ alkyl, —$C_{1-5}$ alkenyl, aryl, heteroaryl, or heterocycle, optionally substituted with one or more of —OH, —SH, C(O)H, COOR$_9$, $C_{1-5}$ acyloxy, halogen, NR$_9$R$_{10}$, $C_{1-5}$ thioether, or $C_{1-5}$ alkoxy; and R$_7$ is as defined above;

13) (a) R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, and pyridine; and (b) the remainder of R$_2$, R$_3$, R$_5$ and R$_6$ are independently selected from (i) hydrogen, (ii) halogen, (iii) NO$_2$, (iv) —CN, (v) —OR$_9$, (vi) —NR$_9$R$_9$, (vii) $C_{1-3}$ acyloxy, (viii) thiol, (ix) COOR$_9$, or (x) —$C_{1-3}$ alkyl, —$C_{1-3}$ alkenyl, aryl, heteroaryl, or heterocycle, optionally substituted with one or more of —OH, —SH, C(O)H, COOR$_9$, $C_{1-5}$ acyloxy, halogen, NR$_9$R$_9$, $C_{1-3}$ thioether, or $C_{1-3}$ alkoxy; and R$_7$ is as defined above;

14) (a) R$_3$ and R$_4$, or R$_4$ and R$_5$, combine to form a fused ring-structure which is cycloalkyl, aryl, or heterocyclic selected from phenyl, cyclopentyl, cyclohexyl, pyrrole, furan, thiophene, pyrazole, or pyridine; and (b) the remainder of $R_2$, $R_3$, $R_5$ and $R_6$ are independently selected from (i) hydrogen, (ii) halogen, (iii) —$OR_9$, (iv) —$NR_9R_9$, (v) thiol, or (vi) —$C_{1-3}$ alkyl or alkenyl optionally substituted with one or more of —OH, —SH, halogen, or $NH_2$; and $R_7$ is as defined above;

15) (a) $R_3$ and $R_4$, or $R_4$ and $R_5$, combine to form a fused ring-structure which is cycloalkyl, aryl, or heterocyclic selected from phenyl, cyclopentyl, cyclohexyl, pyrrole, furan, thiophene, pyrazole, or pyridine; and (b) the remainder of $R_2$, $R_3$, $R_5$ and $R_6$ are independently selected from $C_{1-3}$ alkyl or $OR_9$; and $R_7$ is as defined above;

16) (a) $R_3$ and $R_4$, or $R_4$ and $R_5$, combine to form a fused ring-structure which is cycloalkyl, aryl, or heterocyclic selected from —X—$(CH_2)_{n'}$—X— wherein n' is 1 and X is nitrogen, sulfur, or oxygen; and (b) the remainder of $R_2$, $R_3$, $R_5$ and $R_6$ are independently selected from (i) hydrogen, (ii) halogen, (iii) $NO_2$, (iv) —CN, (v) —$OR_{10}$, (vi) —$NR_9R_{10}$, (vii) $C_{1-5}$ acyloxy, (viii) thiol, (ix) $COOR_9$, or (x) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy; and $R_7$ is as defined above;

17) (a) $R_3$ and $R_4$, or $R_4$ and $R_5$, combine to form a fused ring-structure which is cycloalkyl, aryl, or heterocyclic selected from —X—$(CH_2)_{n'}$—X— wherein n' is 1 and X is nitrogen, sulfur, or oxygen; and (b) the remainder of $R_2$, $R_3$, $R_5$ and $R_6$ are independently selected from (i) hydrogen, (ii) halogen, (iii) $NO_2$, (iv) —CN, (v) —$OR_9$, (vi) —$NR_9R_9$, (vii) $C_{1-3}$ acyloxy, (viii) thiol, (ix) $COOR_9$, or (x) —$C_{1-3}$ alkyl, —$C_{1-3}$ alkenyl, aryl, heteroaryl, or heterocycle, optionally substituted with one or more of —OH, —SH, C(O)H, $COOR_9$, $C_{1-5}$ acyloxy, halogen, $NR_9R_9$, $C_{1-3}$ thioether, or $C_{1-3}$ alkoxy; and $R_7$ is as defined above;

18) (a) $R_3$ and $R_4$, or $R_4$ and $R_5$, combine to form a fused ring-structure which is cycloalkyl, aryl, or heterocyclic selected from —X—$(CH_2)_{n'}$—X— wherein n' is 1 and X is nitrogen, sulfur, or oxygen; and (b) the remainder of $R_2$, $R_3$, $R_5$ and $R_6$ are independently selected from (i) hydrogen, (ii) halogen, (iii) —$OR_9$, (iv) —$NR_9R_9$, (v) thiol, or (vi) —$C_{1-3}$ alkyl or alkenyl optionally substituted with one or more of —OH, —SH, halogen, or $NH_2$; and $R_7$ is as defined above;

19) (a) $R_3$ and $R_4$, or $R_4$ and $R_5$, combine to form a fused ring-structure which is cycloalkyl, aryl, or heterocyclic selected from —X—$(CH_2)_{n'}$—X— wherein n' is 1 and X is nitrogen, sulfur, or oxygen; and (b) the remainder of $R_2$, $R_3$, $R_5$ and $R_6$ are independently selected from $C_{1-3}$ alkyl or $OR_9$; and $R_7$ is as defined above;

20) (a) $R_3$ and $R_4$, or $R_4$ and $R_5$, combine to form a fused ring-structure which is cycloalkyl, aryl, or heterocyclic selected from —$(CH)_{n''}$XH— wherein n'' is 2 and X is nitrogen, sulfur, or oxygen; and (b) the remainder of $R_2$, $R_3$, $R_5$ and $R_6$ are independently selected from (i) hydrogen, (ii) halogen, (iii) $NO_2$, (iv) —CN, (v) —$OR_{10}$, (vi) —$NR_9R_{10}$, (vii) $C_{1-5}$ acyloxy, (viii) thiol, (ix) $COOR_9$, or (x) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy; and $R_7$ is as defined above;

21) (a) $R_3$ and $R_4$, or $R_4$ and $R_5$, combine to form a fused ring-structure which is cycloalkyl, aryl, or heterocyclic selected from —$(CH)_{n''}$XH— wherein n'' is 2 and X is nitrogen, sulfur, or oxygen; and (b) the remainder of $R_2$, $R_3$, $R_5$ and $R_6$ are independently selected from (i) hydrogen, (ii) halogen, (iii) $NO_2$, (iv) —CN, (v) —$OR_9$, (vi) —$NR_9R_9$, (vii) $C_{1-3}$ acyloxy, (viii) thiol, (ix) $COOR_9$, or (x) —$C_{1-3}$ alkyl, —$C_{1-3}$ alkenyl, aryl, heteroaryl, or heterocycle, optionally substituted with one or more of —OH, —SH, C(O)H, $COOR_9$, $C_{1-5}$ acyloxy, halogen, $NR_9R_9$, $C_{1-3}$ thioether, or $C_{1-3}$ alkoxy; and $R_7$ is as defined above;

22) (a) $R_3$ and $R_4$, or $R_4$ and $R_5$, combine to form a fused ring-structure which is cycloalkyl, aryl, or heterocyclic selected from —$(CH)_{n''}$XH— wherein n'' is 2 and X is nitrogen, sulfur, or oxygen; and (b) the remainder of $R_2$, $R_3$, $R_5$ and $R_6$ are independently selected from (i) hydrogen, (ii) halogen, (iii) —$OR_9$, (iv) —$NR_9R_9$, (v) thiol, or (vi) —$C_{1-3}$ alkyl or alkenyl optionally substituted with one or more of —OH, —SH, halogen, or $NH_2$; and $R_7$ is as defined above;

23) (a) $R_3$ and $R_4$, or $R_4$ and $R_5$, combine to form a fused ring-structure which is cycloalkyl, aryl, or heterocyclic selected from —$(CH)_{n''}$XH— wherein n'' is 2 and X is nitrogen, sulfur, or oxygen; and (b) the remainder of $R_2$, $R_3$, $R_5$ and $R_6$ are independently selected from $C_{1-3}$ alkyl or $OR_9$; and $R_7$ is as defined above;

A second series of subembodiments is defined when $R_1$ is $(CH_2)_nSR_7$, n is 0, 1, 2, or 3, $R_7$ is $C_{1-5}$ alkyl optionally substituted with —OH, or $C(O)C_{1-3}$ alkyl; and $R_2$, $R_3$, $R_4$, $R_5$ and $R_6$ are as defined in any one of the 4$^{th}$ through 23d subembodiments of the first series of subembodiments. A subset of the second series of embodiments is defined when $R_1$ is $SR_7$, $R_7$ is $C_{1-5}$ alkyl optionally substituted with —OH, or $C(O)C_{1-3}$ alkyl; $R_4$, is —NHCO—$C_{1-3}$ alkyl; and $R_2$, $R_3$, $R_5$ and $R_6$ are CH.

A third series of subembodiments is defined when $R_1$ is $(CH_2)_nSR_7$, n is 0, 1, 2, or 3, $R_7$ is $C_{1-3}$ alkyl, or $C(O)C_{1-3}$ alkyl; and $R_2$, $R_3$, $R_4$, $R_5$ and $R_6$ are as defined in any one of the 4$^{th}$ through 23d subembodiments of the first series of subembodiments. Preferably, $R_4$, is —NHCO—$C_{1-3}$ alkyl; and $R_2$, $R_3$, $R_5$ and $R_6$ are CH.

A fourth series of subembodiments is defined when $R_1$ is $(CH_2)_nSR_7$, n is 0, 1, 2, or 3, $R_7$ is hydrogen; and $R_2$, $R_3$, $R_4$, $R_5$ and $R_6$ are as defined in any one of the 4$^{th}$ through 23d subembodiments of the first series of subembodiments. Preferably, $R_4$, is —NHCO—$C_{1-3}$ alkyl; and $R_2$, $R_3$, $R_5$ and $R_6$ are CH.

A fifth series of subembodiments is defined when $R_1$ is $SR_7$, $R_7$ is $C_{1-5}$ alkyl optionally substituted with —OH; and $R_2$, $R_3$, $R_4$, $R_5$ and $R_6$ are as defined in any one of the 4$^{th}$ through 23d subembodiments of the first series of subembodiments. Preferably, $R_4$, is —NHCO—$C_{1-3}$ alkyl; and $R_2$, $R_3$, $R_5$ and $R_6$ are CH.

A sixth series of subembodiments is defined when $R_1$ is $SR_7$, $R_7$ is $C_{1-3}$ alkyl; and $R_2$, $R_3$, $R_4$, $R_5$ and $R_6$ are as defined in any one of the 4$^{th}$ through 23d subembodiments of the first series of subembodiments. Preferably, $R_4$, is —NHCO—$C_{1-3}$ alkyl; and $R_2$, $R_3$, $R_5$ and $R_6$ are CH.

A seventh series of subembodiments is defined when $R_1$ is $SR_7$, $R_7$ is hydrogen; and $R_2$, $R_3$, $R_4$, $R_5$ and $R_6$ are as defined in any one of the 4$^{th}$ through 23d subembodiments of the first series of subembodiments. Preferably, $R_4$, is —NHCO—$C_{1-3}$ alkyl; and $R_2$, $R_3$, $R_5$ and $R_6$ are CH.

An eighth series of subembodiments is defined when $R_1$ is $(CH_2)_nNHR_7$, n is 0, 1, 2, or 3, $R_7$ is $C_{1-5}$ alkyl optionally substituted with —OH; and $R_2$, $R_3$, $R_4$, $R_5$ and $R_6$ are as defined in any one of the 4$^{th}$ through 23d subembodiments of the first series of subembodiments.

A ninth series of subembodiments is defined when $R_1$ is $(CH_2)_nNHR_7$, n is 0, 1, 2, or 3, $R_7$ is $C_{1-3}$ alkyl; and $R_2$, $R_3$, $R_4$, $R_5$ and $R_6$ are as defined in any one of the 4$^{th}$ through 23d subembodiments of the first series of subembodiments.

An tenth series of subembodiments is defined when $R_1$ is $(CH_2)_nNHR_7$, n is 0, 1, 2, or 3, $R_7$ is hydrogen; and $R_2$, $R_3$, $R_4$, $R_5$ and $R_6$ are as defined in any one of the 4th through 23d subembodiments of the first series of subembodiments.

An eleventh series of subembodiments is defined when $R_1$ is $NHR_7$, $R_7$ is $C_{1-5}$ alkyl optionally substituted with —OH; and $R_2$, $R_3$, $R_4$, $R_5$ and $R_6$ are as defined in any one of the 4th through 23d subembodiments of the first series of subembodiments.

A twelfth series of subembodiments is defined when $R_1$ is $NHR_7$, $R_7$ is $C_{1-3}$ alkyl; and $R_2$, $R_3$, $R_4$, $R_5$ and $R_6$ are as defined in any one of the 4th through 23d subembodiments of the first series of subembodiments.

A thirteenth series of subembodiments is defined when $R_1$ is $NHR_7$, $R_7$ is hydrogen; and $R_2$, $R_3$, $R_4$, $R_5$ and $R_6$ are as defined in any one of the 4th through 23d subembodiments of the first series of subembodiments.

An fourteenth series of subembodiments is defined when $R_1$ is $OR_7$, $R_7$ is $C_{1-5}$ alkyl optionally substituted with —OH; and $R_2$, $R_3$, $R_4$, $R_5$ and $R_6$ are as defined in any one of the 8th through 23d subembodiments of the first series of subembodiments.

A fifteenth series of subembodiments is defined when $R_1$ is $OR_7$, $R_7$ is $C_{1-3}$ alkyl; and $R_2$, $R_3$, $R_4$, $R_5$ and $R_6$ are as defined in any one of the 8th through 23d subembodiments of the first series of subembodiments.

A sixteenth series of subembodiments is defined when $R_1$ is $OR_7$, $R_7$ is hydrogen; and $R_2$, $R_3$, $R_4$, $R_5$ and $R_6$ are as defined in any one of the 8th through 23d subembodiments of the first series of subembodiments.

A first series of species of the second principal embodiment are defined when $R_1$ is SH or $SC(O)CH_3$, and:
1) $R_2$ is $OCH_3$, and $R_3$, $R_4$, $R_5$ and $R_6$ are CH.
2) $R_3$ is $OCH_3$, and $R_2$, $R_4$, $R_5$ and $R_6$ are CH.
3) $R_4$ is $OCH_3$, and $R_2$, $R_3$, $R_5$ and $R_6$ are CH.
4) $R_5$ is $OCH_3$, and $R_2$, $R_3$, $R_4$ and $R_6$ are CH.
5) $R_6$ is $OCH_3$, and $R_2$, $R_3$, $R_4$ and $R_5$ are CH.
6) 2 of $R_2$, $R_3$, $R_4$, $R_5$, and $R_6$ are $OCH_3$, and the remainder of $R_2$, $R_3$, $R_4$, $R_5$, and $R_6$ are CH.
7) $R_2$ is $SCH_3$, and $R_3$, $R_4$, $R_5$ and $R_6$ are CH.
8) $R_3$ is $SCH_3$, and $R_2$, $R_4$, $R_5$ and $R_6$ are CH.
9) $R_4$ is $SCH_3$, and $R_2$, $R_3$, $R_5$ and $R_6$ are CH.
10) $R_5$ is $SCH_3$, and $R_2$, $R_3$, $R_4$ and $R_6$ are CH.
11) $R_6$ is $SCH_3$, and $R_2$, $R_3$, $R_4$ and $R_5$ are CH.
12) 2 of $R_2$, $R_3$, $R_4$, $R_5$, and $R_6$ are $SCH_3$, and the remainder of $R_2$, $R_3$, $R_4$, $R_5$, and $R_6$ are CH.
13) $R_2$ is $NHC(O)CH_3$, and $R_3$, $R_4$, $R_5$ and $R_6$ are CH.
14) $R_3$ is $NHC(O)CH_3$, and $R_2$, $R_4$, $R_5$ and $R_6$ are CH.
15) $R_4$ is $NHC(O)CH_3$, and $R_2$, $R_3$, $R_5$ and $R_6$ are CH.
16) $R_5$ is $NHC(O)CH_3$, and $R_2$, $R_3$, $R_4$ and $R_6$ are CH.
17) $R_6$ is $NHC(O)CH_3$, and $R_2$, $R_3$, $R_4$ and $R_5$ are CH.

A second series of preferred species are defined when $R_1$ is $NH_2$, and $R_2$, $R_3$, $R_4$, $R_5$ and $R_6$ are as defined in any one of species 1-17 of the first series of preferred embodiments.

A third series of preferred species are defined when $R_1$ is $NHC(O)CH_3$, and $R_2$, $R_3$, $R_4$, $R_5$ and $R_6$ are as defined in any one of species 1-17 of the first series of preferred embodiments.

In a fourth principal embodiment the compounds of the present invention are defined by structures (IV) or (V):

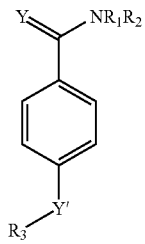

(IV)

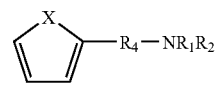

(V)

wherein:
1) $R_1$, $R_2$, and $R_3$ are independently (i) substituted or unsubstituted alkyl, alkenyl, aryl, or heterocycle, (ii) hydrogen, (iii) $C(O)$—$C_{1-3}$ alkyl, or (iv) —$(CH_2)_{1-5}C(O)NR_9R_{10}$;
2) $R_9$ is hydrogen or $C_{1-3}$ alkyl;
3) $R_{10}$ is hydrogen, or $C_{1-5}$ alkyl optionally substituted with —OH;
4) Y and Y' are independently oxygen or sulfur,
5) X is oxygen, sulfur, or nitrogen; and
6) $R_4$ is $C_{1-5}$ alkyl, optionally substituted by —OH, or $NR_9R_9$.

A first series of subembodiments of the fourth principal embodiment are defined by structure (IV) when Y and Y' are as described above, and:
1. $R_1$ is hydrogen, and $R_2$ and $R_3$ are $C_{1-5}$ alkyl optionally substituted with —OH; and
2. $R_1$ is hydrogen, and $R_2$ and $R_3$ are hydrogen or $C_{1-3}$ alkyl.

A second series of subembodiments of the fourth principal embodiment are defined by structure (V) when:
1. X is sulfur, $R_1$ is hydrogen, and $R_2$ is $C_{1-5}$ alkyl optionally substituted with —OH;
2. X is sulfur, $R_1$ is hydrogen, and $R_2$ is hydrogen or $C_{1-3}$ alkyl;
3. X is sulfur, $R_1$ is hydrogen, $R_2$ is $C_{1-5}$ alkyl optionally substituted with —OH; and $R_4$ is unsubstituted $(CH_2)_{1-5}$; or
4. X is sulfur, $R_1$ is hydrogen, $R_2$ is hydrogen or $C_{1-3}$ alkyl, and $R_4$ is unsubstituted $(CH_2)_{1-3}$.

Preferred species are defined for structure (IV) when Y is sulfur, Y' is oxygen, $R_1$ and $R_2$ are hydrogen, and $R_3$ is methyl, and for structure (V) when X is sulfur, $R_4$ is ethylene and $R_1$ and $R_2$ are hydrogen.

The compounds of this invention can be optionally substituted with substituents that do not adversely affect the activity of the compound as a skin lightener. Nonlimiting examples of substituents include, but are not limited to, alkyl (including lower alkyl), heteroalkyl, aryl, heterocyclic (including heteroaryl and heterocycloalkyl), halo, hydroxyl, carboxyl, acyl, acyloxy, amino, alkylamino, arylamino, alkoxy, aryloxy, alkylthio, alkylamido, nitro, cyano, sulfonic acid, sulfate, phosphonic acid, phosphate, or phosphonate, either unprotected, or protected as necessary, as known to those skilled in the air, for example, as taught in Greene, et al., *Protective Groups in Organic Synthesis*, John Wiley and Sons, Second Edition, 1991. It will be understood that the present invention also covers "prodrugs" for such compositions, and pharmaceutically acceptable salts and esters thereof.

Properties of the Compounds of the Present Invention

In the present invention, one or all of three in vitro bioassays can be utilized to evaluate the efficacy and toxicity of candidate skin-lightening compounds. The three bioassays characterize the compounds with regard to mammalian tyrosinase enzyme inhibition (cell free), pigmentation in melanocyte cultured cells, and cytotoxicity of mammalian cultured cells. Both cell-based pigmentation and cell-free enzymatic assays have been developed [5, 6, 25] using the mammalian melanocyte cell line, Mel-Ab, a C57BL/6 mouse-derived cell line that produces high levels of melanin. [21] A distinct advantage of this approach is that humans share substantial sequence similarities in their genes (DNA) and proteins (such as tyrosinase) with mice, relative to non-mammalian species (e.g., mushrooms). So, mouse Mel-Ab melanocytes can serve as adequate surrogates for human melanocytes for many pharmacologic purposes.

These adherent murine melanocytes are grown on tissue culture plastic in medium supplemented with fetal bovine serum, 12-O-tetradecanoylphorbol-13-acetate (TPA) to stimulate cell division via down-regulation of protein kinase C, [22, 23] and cholera toxin to stimulate adenylate cyclase activity in the absence of α-MSH. [15, 24] Cellular lysates of Mel-Ab cells may be used as tyrosinase enzyme preparations. Multi-well plate assays have been validated [5, 6, 25] for enzyme inhibition (e.g., DOPA oxidation by colorimetric measurement or radiolabeled substrate incorporation into melanin) and for pigmentation assays on cultured Mel-Ab cells. After 4 days of treatment of cultured cells, melanin content is determined using a spectrophotometer at 400+ nm. [6, 25] This assay can detect an apparent loss in pigmentation resulting from either inhibition of de novo synthesis (e.g. via inhibition of tyrosinase, or the adenylate cyclase pathway, or another pathway) or a cytostatic/cytotoxic mechanism. It is therefore a broad primary screen. It is used in parallel with the tyrosinase enzymatic assay to determine whether an inhibitor of pigmentation at the cellular level is acting primarily at the enzyme level.

To determine cytotoxicity, crystal violet or other staining methods may be used to quantify adherent cell numbers following a period of treatment by an agent HQ is typically used as a positive control in the assay, since it exhibits an $IC_{50}$ in the low micrograms per milliliter range on Mel-Ab culture using this assay, albeit owing to cytotoxicity and not inhibition of pigmentation per se. [6] It should be noted that many inhibitors identified in cell-free enzymatic assays might have subsequent difficulties with toxicity or delivery in melanocyte cell-based assays. Therefore, all three in vitro assays in combination provide an excellent characterization of candidate skin lightening compounds.

A distinct advantage of the screening systems (developed by the inventors of the present invention) is the focus on mammalian tyrosinase, as opposed to non-mammalian enzymes often used by other investigators, such as mushroom tyrosinase. Since the biochemical and pharmacologic characteristics of an enzyme or isozyme can vary dramatically between species of organisms (e.g., due to dissimilarities in primary, secondary, and tertiary structure), it is highly preferable that candidate topical skin lighteners intended for human use be discovered based on their biochemical action against a mammalian source of the enzyme. Mushroom tyrosinase (and in some instances plant polyphenol oxidases) has been used in the vast majority of prior inhibitor studies. [28, 29] Yet fungal tyrosinase exhibits substantial dissimilarities from mammalian tyrosinase(s), and is viewed as a substantially inferior strategy for pharmacologic screening. Thus, the methods reported by the inventors of the present invention for screening against mammalian tyrosinase or within melanocytes is highly preferred over other possible screening strategies. [5, 6, 25]

The substrate kinetic "affinity" of mammalian tyrosinase for L-tyrosine is approximately $K_M$=600 μM. A potentially effective candidate skin lightening agent is considered to be desirable, active, and/or functional if it renders 50% inhibition of mammalian tyrosinase enzyme activity, at concentrations below half the enzyme's "affinity" for tyrosine in cell-free enzyme extracts ($IC_{50} \leq 300$ μM) and pigment production in melanocyte cell cultures ($IC_{50} \leq 300$ μM). In preferred embodiments the agent has an $IC_{50}$ against tyrosinase in cell-free enzyme extracts of less then 200, 100, 50, or 25 μM, and/or an $IC_{50}$ against pigment production in melanocyte cell cultures of less than 200, 100, 50, or 25 μM. In addition, it is desirable for the compounds to exhibit minimal cytotoxicity, e.g., thus retaining viability of 50% or more of the cultured cells ($IC_{50} \geq 300$ μM), as evidenced by adherent cell number. In preferred embodiments the agent exhibits toxicity at greater than 500, 750, or 1000 μM.

Curto, E. V., et al. (1999) [25] reports that methyl gentisate is an "effective" candidate skin-lightening agent based on in vitro bioassays, because it has an $IC_{50}$ of 11.2±4 (ug/mL) against tyrosinase activity in cell-free assays, an $IC_{50}$ of 30.9±5 (ug/mL) in melanocyte cell cultures, and melanocyte cytotoxicity $IC_{50}$ of 118.7±12 (ug/mL). Methyl gentisate thus poses a standard, against which the efficacy and cytotoxicity of other tyrosinase inhibiting compounds can be evaluated. By contrast to MG, hydroquinone is an inferior standard, exhibiting potent cytotoxicity and minimal enzymatic inhibition. [5, 6, 25]

Significantly, many of the particular compounds of this invention are comparable to or a more effective candidate skin lightening agents than methyl gentisate. Thus, in another embodiment the invention provides methods for inhibiting pigment production that includes administering an effective treatment amount of a pigment inhibiting compound wherein (i) the compound inhibits tyrosinase activity equivalent to or greater than methyl gentisate in cell-free enzyme extracts from mammalian melanocyte or melanoma cells, when evaluated using either a colormetric DOPA oxidation or a radiolabeled tyrosine or DOPA substrate assay as described in Curto, E. V., et al. (1999) [25], or (ii) the compound inhibits de novo pigment production (synthesis and/or accumulation) equivalent to or greater than methyl gentisate when evaluated in cultured mammalian melanocyte or melanoma cells. Curto, E. V., et al. (1999) [25]. In a preferred embodiment the toxicity of the compound in mammalian melanocyte, melanoma, or other cell cultures is equivalent to or less than the toxicity of methyl gentisate. Curto, E. V., et al. (1999) [25].

In another embodiment computer-based molecular orbital predictions can aid in the understanding and predictability of structure-activity relationships, such that other effective compounds can be identified and evaluated. See Sakurada, J., et al., "Kinetic and molecular orbital studies on the rate of oxidation of monosubstituted phenols and anilines by horseradish peroxidase compound II." Biochemistry 29: 4093-4098 (1990) [26].

DEFINITIONS AND USE OF TERMS

The following definitions and term construction are intended, unless otherwise indicated:

Specific and preferred values listed below for radicals, substituents, and ranges, are for illustration only; they do not exclude other defined values or other values within defined ranges for the radicals and substituents.

Halo is fluoro, chloro, bromo, or iodo.

Alkyl, alkoxy, alkenyl, alkynyl, etc. denote both straight and branched groups; but reference to an individual radical such as "propyl" embraces only the straight chain radical, a branched chain isomer such as "isopropyl" being specifically referred to.

The term alkyl, as used herein, unless otherwise specified, refers to a saturated straight, branched, or cyclic, primary, secondary, or tertiary hydrocarbon of $C_1$ to $C_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. When the context of this document allows alkyl to be substituted, the moieties with which the alkyl group can be substituted are selected from the group consisting of hydroxyl, amino, alkylamino, arylamino, alkoxy, aryloxy, aryl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a $C_1$ to $C_4$ saturated straight, branched, or if appropriate, a cyclic (for example, cyclopropyl) alkyl group, including both substituted and unsubstituted forms. Unless otherwise specifically stated in this application, when alkyl is a suitable moiety, lower alkyl is preferred. Similarly, when alkyl or lower alkyl is a suitable moiety, unsubstituted alkyl or lower alkyl is preferred.

The terms alkenyl and alkynyl refer to alkyl moieties, including both substituted and substituted forms, wherein at least one saturated C—C bond is replaced by a double or triple bond. Thus, $(C_2-C_6)$alkenyl can be vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, or 5-hexenyl. Similarly, $(C_2-C_6)$alkynyl can be ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, or 5-hexynyl.

The term "alkylene" refers to a saturated, straight chain, divalent alkyl radical of the formula $-(CH_2)_n-$, wherein n can be 1, 2, 3, 4, 5, 6, 7, 8, 9, or 10.

As used herein, with exceptions as noted, "aryl" is intended to mean any stable monocyclic, bicyclic or tricyclic carbon ring of up to 8 members in each ring, wherein at least one ring is aromatic as defined by the Huckel 4n+2 rule. Examples of aryl ring systems include phenyl, naphthyl, tetrahydronaphthyl, and biphenyl. The aryl group can be substituted with one or more moieties selected from the group consisting of hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The term heterocycle or heterocyclic, as used herein except where noted represents a stable 5- to 7-membered monocyclic or stable 8- to 11-membered bicyclic heterocyclic ring which is either saturated or unsaturated, including heteroaryl, and which consists of carbon atoms and from one to three heteroatoms selected from the group consisting of N, O, S, and P; and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure.

Nonlimiting examples of heteroaryl and heterocyclic groups include furyl, furanyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbazolyl, oxazolyl, thiazolyl, isothiazolyl, 1,2,4-thiadiazolyl, isooxazolyl, pyrrolyl, quinazolinyl, cinnolinyl, phthalazinyl, xanthinyl, hypoxanthinyl, thiophene, furan, pyrrole, isopyrrole, pyrazole, imidazole, 1,2,3-triazole, 1,2,4-triazole, oxazole, isoxazole, thiazole, isothiazole, pyrimidine or pyridazine, and pteridinyl, aziridines, thiazole, isothiazole, 1,2,3-oxadiazole, thiazine, pyridine, pyrazine, piperazine, pyrrolidine, oxaziranes, phenazine, phenothiazine, morpholinyl, pyrazolyl, pyridazinyl, pyrazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, pyrazolopyrimidinyl, adenine, N6-alkylpurines, N6-benzylpurine, N6-halopurine, N6-vinypurine, N6-acetylenic purine, N6-acyl purine, N6-hydroxyalkyl purine, N6-thioalkyl purine, thymine, cytosine, 6-azapyrimidine, 2-mercaptopyrmidine, uracil, N5-alkyl-pyrimidines, N5-benzylpyrimidines, N5-halopyrimidines, N5-vinyl-pyrimidine, N5-acetylenic pyrimidine, N5-acyl pyrimidine, N5-hydroxyalkyl purine, and N6-thioalkyl purine, and isoxazolyl. The heteroaromatic and heterocyclic moieties can be optionally substituted as described above for aryl, including substituted with one or more substituents selected from hydroxyl, amino, alkylamino, arylamino, alkoxy, aryloxy, alkyl, heterocycle, halo, carboxy, acyl, acyloxy, amido, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991.

The heteroaromatic can be partially or totally hydrogenated as desired. As a nonlimiting example, dihydropyridine can be used in place of pyridine. Functional oxygen and nitrogen groups on the heteroaryl group can be protected as necessary or desired. Suitable protecting groups are well known to those skilled in the art, and include trimethylsilyl, dimethylhexylsilyl, t-butyldi-methylsilyl, and t-butyldiphenylsilyl, trityl or substituted trityl, alkyl groups, acyl groups such as acetyl and propionyl, methanesulfonyl, and p-toluenesulfonyl.

The term acyl refers to a carboxylic acid ester in which the non-carbonyl moiety of the ester group is selected from straight, branched, or cyclic alkyl or lower alkyl, alkoxyalkyl including methoxymethyl, aralkyl including benzyl, aryloxyalkyl such as phenoxymethyl, aryl including phenyl optionally substituted with halogen, $C_1$ to $C_4$ alkyl or $C_1$ to $C_4$ alkoxy, sulfonate esters such as alkyl or aralkyl sulphonyl including methanesulfonyl, the mono, di or triphosphate ester, trityl or monomethoxytrityl, substituted benzyl, trialkylsilyl (e.g. dimethyl-t-butylsilyl) or diphenylmethylsilyl. Aryl groups in the esters optimally comprise a phenyl group. The term "lower acyl" refers to an acyl group in which the non-carbonyl moiety is lower alkyl.

The term alkoxy, as used herein, and unless otherwise specified, refers to a moiety of the structure —O-alkyl, wherein alkyl is as defined above.

Synthetic Methods

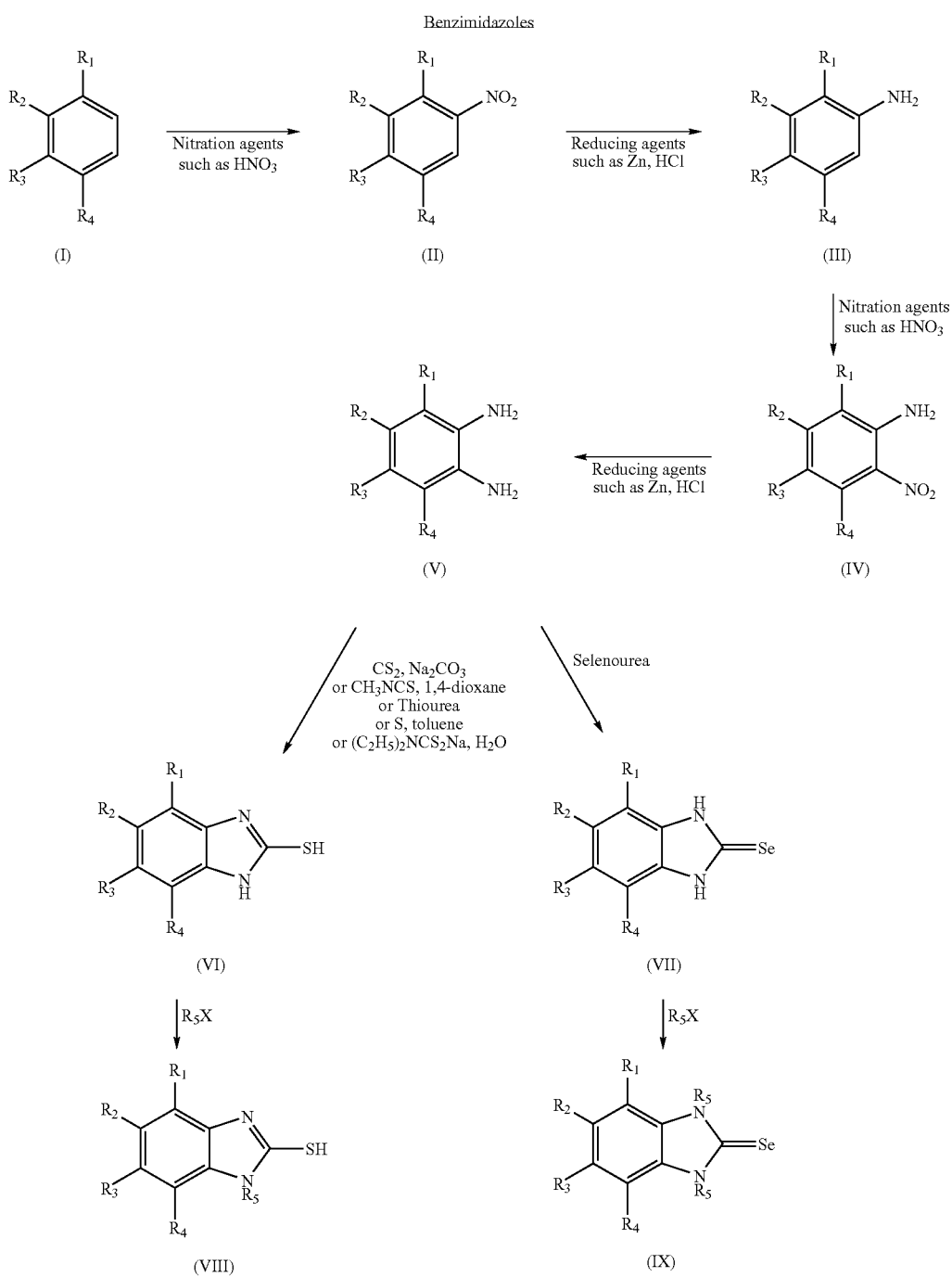

Precursor: Mono- or multiple-substituted benzene. Most are commercially available or can be easily prepared from commercial compounds. The definition of benzene ring substituents $R_1$, $R_2$, $R_3$ and $R_4$ is given in formulas (I) and (II) in section of Summary of The Invention.

Reactants: Nitric acid, Zinc, Hydrochloric acid, Carbon disulfide, Methyl isothiocyanate, Thiourea, Sulfur, Sodium diethyldithiocarbamate, Selenourea.

Solvents: 1,4-Dioxane, Toluene, Pyridine, Dichloromethane, Tetrahydrofuran, Water.

References: Saxena, D. B.; Khajuria, R K; Suri, O. P. Synthesis and Spectral Studies of 2-Mercaptobenzimidazole Derivatives. *J. Heterocycl. Chem.*, 19, 681-683, (1982).

The 1,2-phenylenediamine derivatives (V) can be prepared by twice nitration/reduction reactions on substituted benzene (I), some substituents may need protection under above reaction conditions. Cyclization of (V) with $CS_2$, or $CH_3NCS$, or thiourea, or S, or $(C_2H_5)_2NCS_2Na$ can give the desired 2-mercaptobenzimidazole derivatives (VI). Reaction of (VI) with $R_5X$ ($R_5$ can be alkyl or acyl group; X is Cl, Br, I) can produce alkylated products (VIII). 2-Benzimidazoline-selenium derivatives (VIII) and (IX) can be synthesized similarly by reacting selenourea with (V).

Precursor: Substituted benzene. Most are commercially available or can be easily prepared from commercial compounds. The definition of benzene ring substituents $R_1$, $R_2$, $R_3$, $R_4$ and $R_5$ is given in formulas (I) and (II) in section of Summary of The Invention.

Reactants: Nitric acid, Zinc, Hydrochloric acid, Ammonium thiocyanate, Potassium thiocyanate, Potassium selenocyanate.

Solvents: Acetonitrile, Pyridine, Dichloromethane, Tetrahydrofuran, Water.

References: Rasmussen, C. R; Villani, F. J., Jr.; Weaner, L. E.; Reynolds, B. E.; Hood, A. R; Hecker, L. R—; Nortey, S. O.; Hanskin, A.; Costanzo, M. J.; et al. Improved Procedures for the Preparation of Cycloalkyl-, and Arylalkyl-, and Arylthioureas. *Synthesis,* 6, 456-459, (1988).

Various arylthiourea compounds (IV) can be prepared by reaction of corresponding aniline (III) with $NH_4SCN$ or KSCN in aqueous HCl solution. Alkylation of (I) by $R_6X$ ($R_6$ can be alkyl or acyl group; X is Cl, Br, I) can yield monoalkylated product (VI). By replacing KSCN with KSeCN, the selenium analogous (V) can also be prepared.

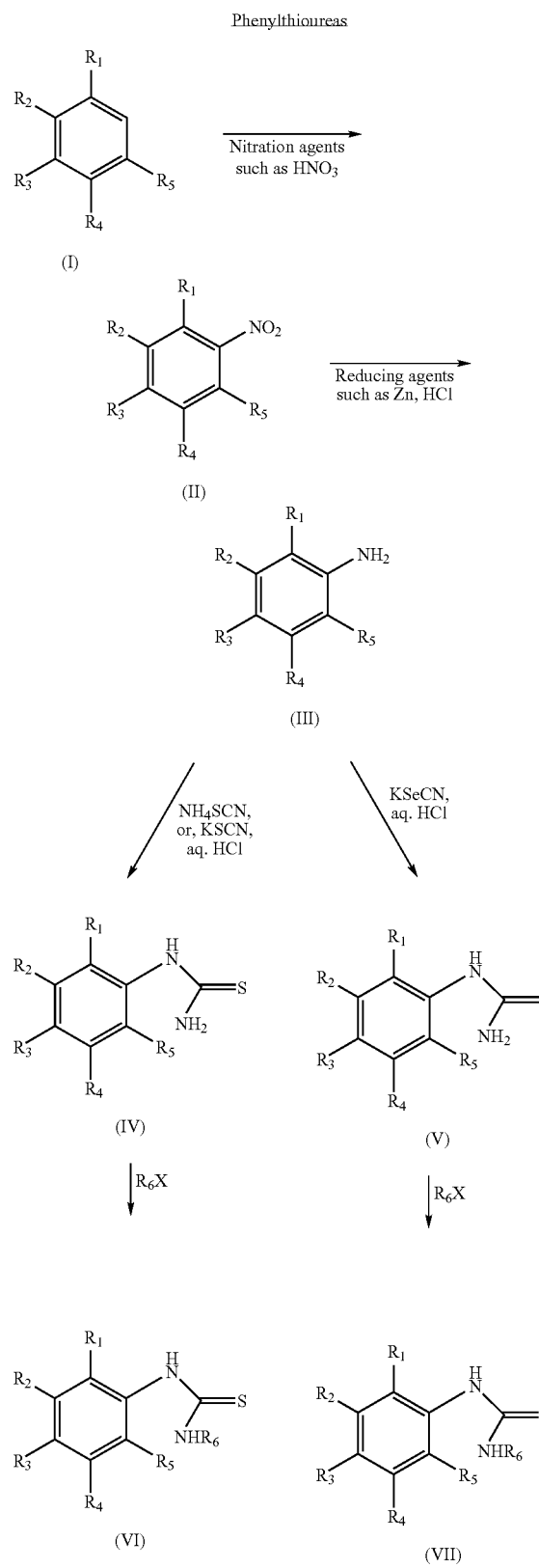

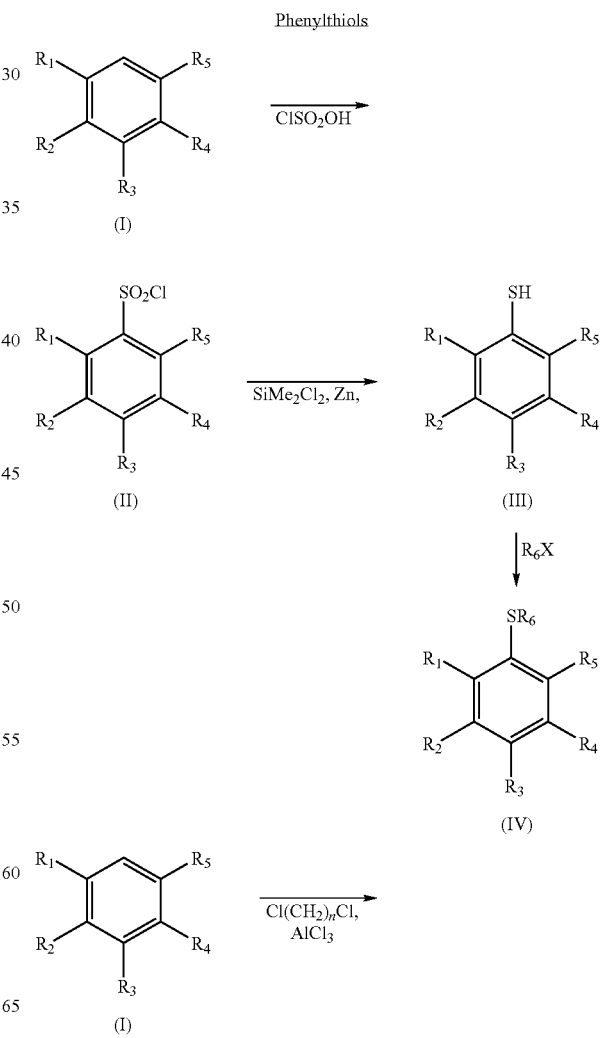

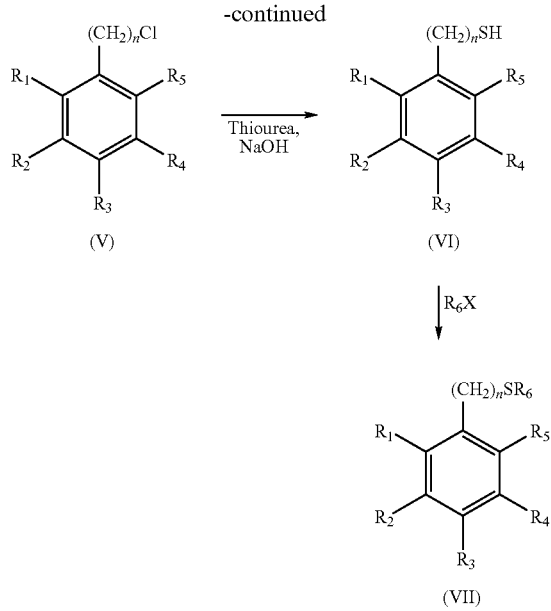

Precursor: Substituted benzene. Most are commercially available or can be easily prepared from commercial compounds. The definition of benzene ring substituents $R_1$, $R_2$, $R_3$, $R_4$ and $R_5$ is given in formulas (I) and (II) in section of Summary of The Invention.

Reactants: Chlorosulfonic acid, Dichlorodimethylsilane, Zinc, $Cl(CH_2)_nCl$ (n is 1-3), Aluminum chloride, Thiourea, Sodium hydroxide.

Solvents: Tetrahydrofuran, Benzene, Dimethyl sulfoxide, Water.

References: Uchiro, H.; Kobayashi, S. Non-aqueous Reduction of Aromatic Sulfonyl Chlorides to Thios Using a Dichlorodimethylsilane-zinc-dimethylacetamide System. *Tetrahedron Lett.*, 40, 3179-3182, (1999).

Substituted arylsulfonyl chlorides (I) can be easily prepared from substituted aromatic compounds (I) by reaction with excess chlorosulfonic acid. Reduction of (II) with dichlorodimethylsilane/zinc will give desired phenylthiole derivatives (III). The substituted phenylalkyl mercaptans (VI) can be prepared from the corresponding chloro compounds (V) which can be obtained from alkylation reaction of (I) (Friedel-Crafts reaction). Both thiole compounds (III) and (VI) can react with alkyl halide $R_6X$ to form the corresponding sulfides (IV) and (VII).

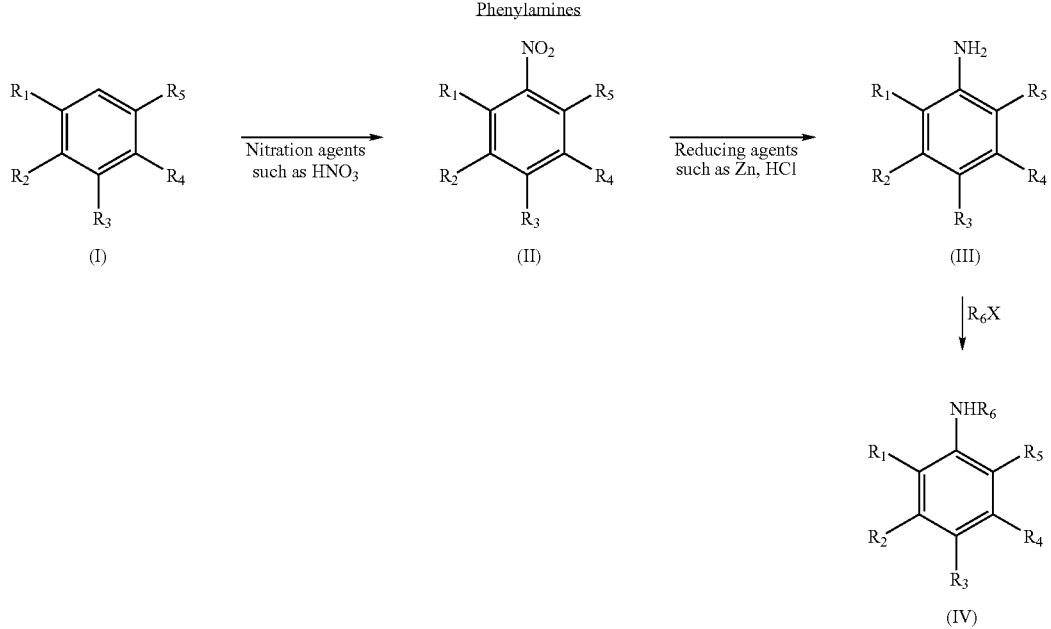

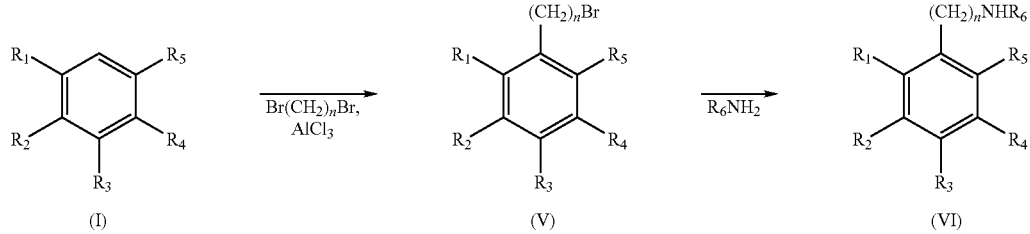

Precursor: Substituted benzene. Most are commercially available or can be easily prepared from commercial compounds. The definition of benzene ring substituents $R_1$, $R_2$, $R_3$, $R_4$ and $R_5$ is given in formulas (I) and (II) in section of Summary of The Invention Reactants: Nitric acid, Zinc, Hydrochloric acid, $Br(CH_2)_nBr$ (n is 1-3), Aluminum chloride.

Solvents: Benzene, Tetrahydrofuran, Diethyl ether, Water.

The preparation of products (II), (IV) and (V) is same as described previously. Reaction of (V) with alkyl amine $R_6NH_2$ ($R_6$ is hydrogen or alkyl) can give arylalkylamine derivatives (VI).

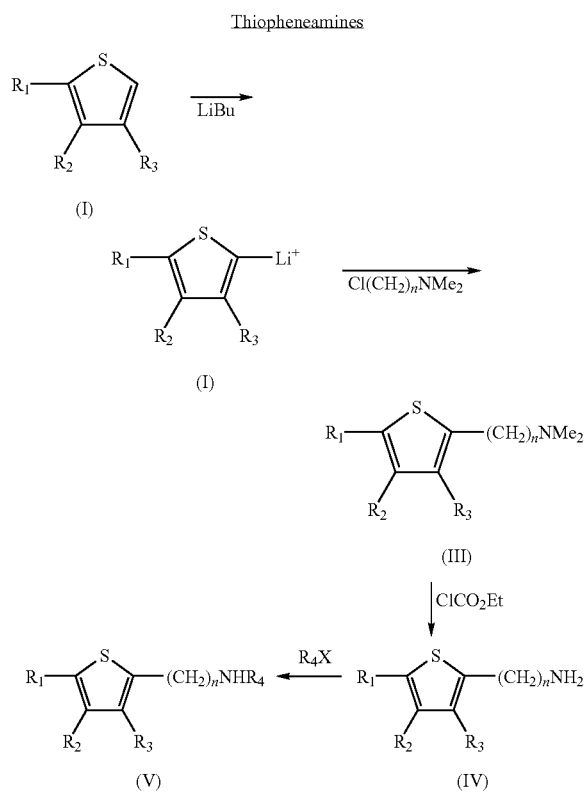

Precursor: Substituted thiophene. Most are commercially available or can be easily prepared from commercial sources. The definition of ring substituents $R_1$, $R_2$ and $R_3$ is same as that given in formulas (I) and (II) in section of Summary of The Invention.

Reactants: Butyllithium, $Cl(CH_2)_nNMe_2$ (n is 1-3), Ethyl chloroformate.

Solvents: Diethyl ether, Tetrahydrofuran, Benzene.

References: Hallberg, A.; Gronowitz, S. On The Reaction of Some Thienyllithium Derivatives with 1-Chloro-2-dimethylaminoethane. *Chem. Scr.,* 16, 42-46, (1980).

Reaction of substituted thiophene with butyllithium can yield 2-thienyllithium salt (II), protection may be necessary for some substituents. Substituted 2-thiophenealkylamine (III) can be prepared by reaction of (a) with 1-chloro-2-dimethylaminoalkane. The products (III), (V) and (V) can be converted to each other by alkylation/dealkylation reactions using alkyl halide $R_4X$ and $ClCO_2Et$, respectively.

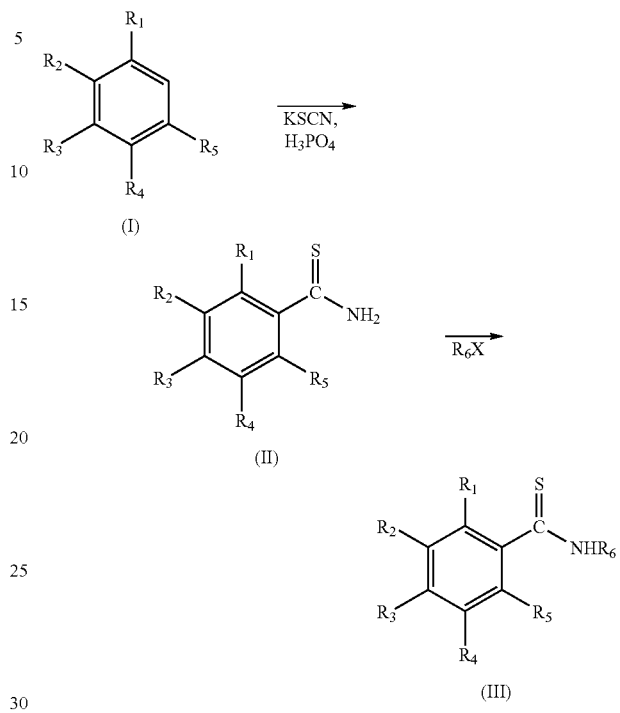

Precursor: Substituted benzene. Most are commercially available or can be easily prepared from commercial compounds. The definition of benzene ring substituents $R_1$, $R_2$, $R_3$, $R_4$ and $R_5$ is given in formulas (I) and (II) in section of Summary of The Invention Reactants: Potassium thiocyanate, Polyphosphoric acid, Sulfuric acid.

Solvents: Benzene, Water.

References: Sastry, S.; Kudav, N. A. One-step Synthesis of Aromatic Thio Amides: Reaction of Aromatic Compounds with Potassium Thiocyanate in Polyphosphoric Acid or Sulfuric Acid. *Indian J. Chem., Sect B,* 18B, 455, (1979).

Benzothioamide derivatives (II) can be prepared from substituted benzene (I) in one single step by reaction with KSCN in polyphosphoric acid or sulfuric acid. The alkylated product (III) can be obtained by using alkyl halide $R_6X$ (X is Cl, Br, I).

Pharmaceutical Formulations and Dosing Regimes

In one embodiment, a compound of this invention is applied or administered to the skin during an appropriate period and using a sufficient number of dosages to achieve skin lightening. The concentration of active compound in the composition will depend on absorption, inactivation, and excretion rates of the compound as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the concentration ranges set forth herein are exemplary only and are not intended to limit the scope or practice of the claimed composition. The active ingredient may be administered as a single dose, or may be divided into a number of smaller doses to be administered at varying intervals of time.

Topical and other formulations of these active and/or functional compounds are of utility in lightening skin pigmentation in humans and other animals. These formulations may be useful for pure cosmetic purposes, simply to obtain a lighter skin color for perceived beautification. The formulations also have medicinal value and can, for example, decrease hyperpigmentation of melasma, age spots, freckles, and other skin blemishes. The compounds of this invention act primarily by inhibiting mammalian melanocyte tyrosinase, the rate-limiting enzyme in the production of melanin from tyrosine and DOPA. Some compounds also absorb ultraviolet radiation (UVR), and may thus protect skin from UVR and photoaging. In addition, some compounds may be antioxidants that protect skin from oxidative damage, and/or may prevent oxidative decomposition of product formulations.

If desirable these formulations could also be used to reduce pigmentation in hair, albeit during the biosynthesis of hair, by blocking pigment production within the melanocytes of hair follicles. The formulations would likely not affect the already emerged pigmented portions of hair, unlike a bleaching agent.

The formulations useful in the present invention contain biologically effective amounts of the functional and/or active compound(s). A biologically effective amount of the active compound is understood by those skilled in the art to mean that a sufficient amount of the compound in the composition is provided such that upon administration to the human or animal by, for example, topical route, sufficient active agent is provided on each application to give the desired result. However, the biologically effective amount of the active compound is at a level that it is not toxic to the human or animal during the term of treatment. By a suitable biologically compatible carrier, when the compound is topically applied, it is understood that the carrier may contain any type of suitable excipient in the form of cosmetic compositions, pharmaceutical adjuvants, sunscreen lotions, creams, and the like. In one embodiment the active compound is administered in a liposomal carrier.

The active compound is administered for a sufficient time period to alleviate the undesired symptoms and the clinical signs associated with the condition being treated, or to achieve the level of desired skin lightening. The individual dosage, dosage schedule, and duration of treatment may be determined by clinical evaluations by those of skill in the art.

Solutions or suspensions for topical application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates; and agents for the adjustment of tonicity such as sodium chloride or dextrose. pH can be adjusted with acids or bases, such as hydrochloric acid or sodium hydroxide.

Suitable vehicles, carriers, or formulations for topical application are known, and include lotions, suspensions, ointments, oil-in-water emulsions, water-in-oil emulsions, creams, gels, tinctures, sprays, powders, pastes, and slow-release transdermal or occlusive patches. Thickening agents, emollients, and stabilizers can be used to prepare topical compositions. Examples of thickening agents include petrolatum, beeswax, xanthan gum, or polyethylene glycol, humectants such as sorbitol, emollients such as mineral oil, lanolin and its derivatives, or squalene. A number of solutions and ointments are commercially available, especially for dermatologic applications.

The compounds can be provided in the form of pharmaceutically-acceptable salts. As used herein, the term "pharmaceutically-acceptable salts or complexes" refers to salts or complexes that retain the desired biological activity of the parent compound and exhibit minimal, if any, undesired toxicological effects. Examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acids, naphthalenedisulfonic acids, and polygalacturonic acid; (b) base addition salts formed with polyvalent metal cations such as zinc, calcium, bismuth, barium, magnesium, aluminum, copper, cobalt, nickel, cadmium, and the like, or with an organic cation formed from N,N-benzylethylene-diamine or ethylenediamine; or (c) combinations of (a) and (b); e.g., a zinc tannate salt or the like.

The compounds can be modified in order to enhance their usefulness as pharmaceutical compositions. For example, it is well know in the art that various modifications of the active molecule, such as alteration of charge, can affect water and lipid solubility and thus alter the potential for percutaneous absorption. The vehicle, or carrier, can also be modified to enhance cutaneous absorption, enhance the reservoir effect, and minimize potential irritancy or neuropharmacological effects of the composition. See, in general, Arndt, et al. [27].

Thus, the invention provides various formulations as topical skin lighteners containing the active and/or functional compounds described above. The invention further provides formulations as topical anti-oxidants containing the active and/or functional compounds described above. In still another embodiment the invention provides formulations as topical sunscreens containing the active and/or functional compounds described above. Such formulations can be made in combination with other active and/or functional ingredients used in skincare products (e.g. organic or inorganic sunscreen, antioxidant, anti-inflammatory, anti-erythema, antibiotic, antimicrobial, humectant, or other ingredients). Other ingredients can be formulated with the compounds to augment their effect, including but not limited to Vitamin C, Vitamin E, magnesium ascorbyl phosphate, aloe vera extract, and retinoic acids. In addition, alpha-hydroxy acids can be included to speed up the skin lightening process by exfoliating surface colored skin.

The compounds of the present invention can also be formulated for alternative routes of administration other than topical application, including but not limited to general systemic, oral, intradermal, transdermal, occlusive patches, intravenous, or parenteral administration, and pharmaceutical compositions known generally to those skilled in the art.

The compounds can also be formulated along with other active and/or functional ingredients used in skincare products, depending on the intended use of the formulation. For example, the compounds can be formulated with organic or inorganic sunscreens, an antioxidant, an anti-inflammatory, an anti-erythema, an antibiotic, an antimicrobial, a humectant, or other ingredients.

The active and/or functional compounds described above may also be of use in inhibiting tyrosinase-like enzymes from non-mammalian species, for instance for use in the food science industry for the inhibition of enzymatic browning. [28, 29] Inhibition of plant polyphenol oxidases by agents described here may coincidentally have activity against these non-mammalian enzymes.

Suitable formulations for spraying or treatment of fruits are known generally to those skilled in the art Treatment by these formulations containing the enzyme inhibitors of the present invention might improve shelf life of plant or fungal foods.

EXAMPLES

Example 1

Benzoimidazolethiols

A first class of compounds based upon the template compound benzimidazolethiol (lower left structure) were tested for tyrosinase inhibition, cell culture pigment inhibition, and toxicity, by methods described in Curto, E. V., et al. (1999) [25]. Results of the tests are given in Table 1.

TABLE 1

| ID # | $R_1$ | $R_2$ | $R_3$ | $R_5$ | $R_6$ | R | E | P | T | $\epsilon$ | $\lambda_{max}$ |
|---|---|---|---|---|---|---|---|---|---|---|---|
| 138 | NH | SH | N | H | H | C | 0.25 | — | — | 14300 | 300 |
| 140 | NH | SH | N | CH3 | H | C | 0.12 | 2.4 | >1000 | 6300 | 305 |
| 084 | NH | SH | N | OCH$_3$ | H | C | 0.07 | 1.6 | >1000 | 10000 | 310 |
| 040 | S | SH | N | H | H | C | 8 | — | — | | |
| 091 | S | SH | N | H | OCH$_2$CH$_3$ | C | >1000 | >1000 | >1000 | | |
| 205 | NH | =S | N(CO)CH$_3$ | H | H | C | 0.5 | 8.3 | 35 | | |
| 098 | NH | =Se | NH | H | H | C | 0.8 | 14 | 132 | | |
| 135 | NH | =S | NH | H | H | N | 4 | 256 | >1000 | | |

*Inhibition [µM] as measured in three assays.
Here "E" is the concentration of compound that produces 50% pigment inhibition in the cell-free mammalian-enzyme assay system.
"P" is for the concentration of compound that produces 50% inhibition in the mammalian-melanocyte-culture pigment assay system.
"T" is the concentration of compound that kills 50% of cells in the mammalian-melanocyte-culture toxicity assay system.
The compound extinction coefficient if $\epsilon$ [OD/M × cm] at the wavelength of maximum absorbency $\lambda_{max}$ [nm].

Example 2

Thiophenols

A second class of compounds based upon the template compound benzenethiol were tested for tyrosinase inhibition, cell culture pigment inhibition, and toxicity, by methods described in Curto, E. V., et al. (1999) [25]. Results of the tests are given in Table 2.

TABLE 2

| ID # | $R_1$ | $R_2$ | $R_3$ | $R_4$ | $R_5$ | E | P | T | $\epsilon$ | $\lambda_{max}$ |
|---|---|---|---|---|---|---|---|---|---|---|
| 099 | H | H | OCH$_3$ | H | H | 53 | 85 | 202 | 3000 | 265 |
| 102 | H | H | H | SCH$_3$ | H | 0.24 | 115 | 126 | 2300 | 280 |
| 083 | H | H | H | NH(CO)CH$_3$ | H | 19 | 82 | 542 | 4700 | 265 |

TABLE 2-continued

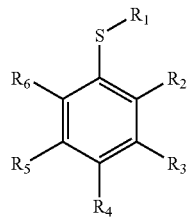

| ID # | R₁ | R₂ | R₃ | R₄ | R₅ | E | P | T | ε | λ$_{max}$ |
|---|---|---|---|---|---|---|---|---|---|---|
| 103 | H | H | OCH₃ | OCH₃ | H | 8 | 8 | >1000 | 4300 | 250 |
| 093 | H | OCH₃ | H | H | OCH₃ | 500 | 200 | 200 | 2700 | 305 |
| 148 | (CO)CH₃ | H | H | NH(CO)CH₃ | H | 500 | 30 | 125 | 3300 | 255 |

*Inhibition [μM] as measured in three assays.
Here "E" is the concentration of compound that produces 50% pigment inhibition in the cell-free mammalian-enzyme assay system.
"P" is for the concentration of compound that produces 50% inhibition in the mammalian-melanocyte-culture pigment assay system.
"T" is the concentration of compound that kills 50% of cells in the mammalian-melanocyte-culture toxicity assay system.
The compound extinction coefficient is ε [OD/M × cm] at the wavelength of maximum absorbency λ$_{max}$ [nm].

Example 3

Phenylthioureas

A third class of compounds based upon the template compound phenylthiourea (lower left structure) were tested for tyrosinase inhibition, cell culture pigment inhibition, and toxicity, by methods described in Curto, E. V., et al. (1999) [25]. Results of the tests are given in Table 3.

TABLE 3

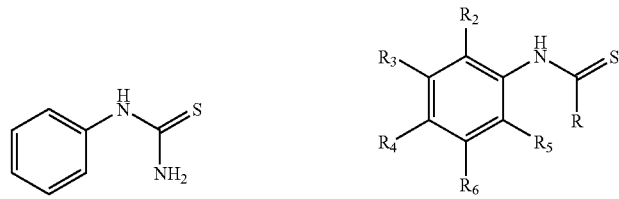

| ID # | R₂ | R₃ | R₄ | R₅ | R | E | P | T | ε | λ$_{max}$ |
|---|---|---|---|---|---|---|---|---|---|---|
| 033 | H | H | H | H | NH₂ | 2 | 12 | >1000 | | |
| 181 | OCH₃ | H | H | H | NH₂ | >1000 | | >1000 | | |
| 105 | H | F | H | H | NH₂ | 1.52 | 1.78 | >1000 | 11000 | 255 |
| 104 | H | OH | H | H | NH₂ | 4 | 8 | >1000 | | |
| 131 | H | CH₃ | H | H | NH₂ | 0.82 | 2.28 | >1000 | | |
| 053 | H | H | OCH₃ | H | NH₂ | 8 | 30 | 60 | | |
| 049 | H | H | NH(CS)NH₂ | H | NH₂ | 4 | 250 | >1000 | | |
| 101 | H | CH₃ | H | CH₃ | NH₂ | 250 | 125 | >1000 | | |
| 054 | H | H | H | H | CH₃ | 16 | 16 | >1000 | | |

*Inhibition [μM] as measured in three assays.
Here "E" is the concentration of compound that produces 50% pigment inhibition in the cell-free mammalian-enzyme assay system.
"P" is for the concentration of compound that produces 50% inhibition in the mammlian-melanocyte-culture pigment assay system.
"T" is the concentration of compound that kills 50% of cells in the mammalian-melanocyte-culture toxicity assay system.
The compound extinction coefficient is ε [OD/M × cm] at the wavelength of maximum absorbency λ$_{max}$ [nm].

Example 4

Miscellaneous

A fourth group of miscellaneous compounds of diverse structure were also tested for tyrosinase inhibition, cell culture pigment inhibition, and toxicity, by methods described in Curto, E. V., et al. (1999) [25]. Results of the tests are given in Table 4.

TABLE 4

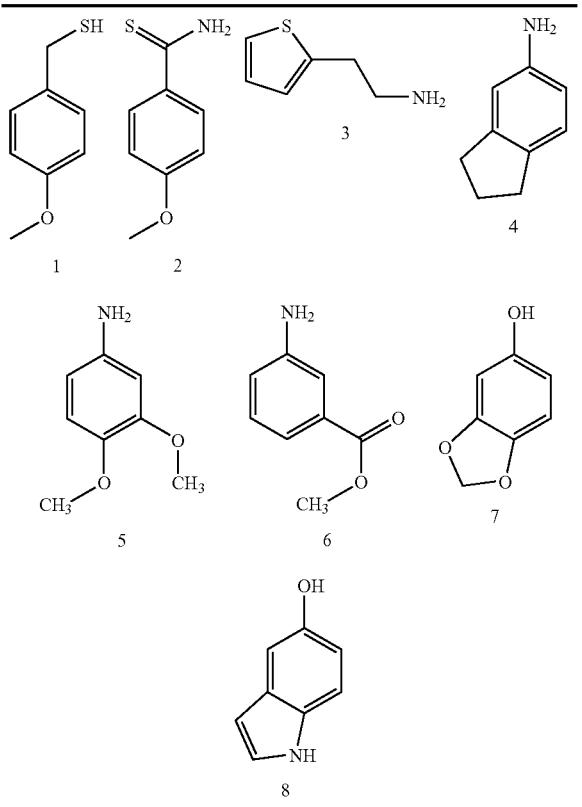

| # | ID # | E | P | T | ε | $\lambda_{max}$ |
|---|------|---|---|---|---|-----------------|
| 1 | 081 | 5 | 81 | 500 | 1000 | 275 |
| 2 | 100 | 32 | 62 | >1000 | | |
| 3 | 073 | >1000 | 100 | >1000 | | |
| 4 | 079 | 73 | 71 | 472 | | |
| 5 | 006 | 110 | 182 | >1000 | | |
| 6 | 092 | 79 | 236 | >1000 | | |
| 7 | 009 | 98 | 209 | 775 | | |
| 8 | 026 | 54 | 153 | 367 | | |

*Inhibition [μM] as measured in three assays.
Here "E" is the concentration of compound that produces 50% pigment inhibition in the cell-free mammalian-enzyme assay system.
"P" is for the concentration of compound that produces 50% inhhibition in the mammalian-menanocyte-culture pigment assay system.
"T" is the concentration of compound that kills 50% of cells in the mammalian-melanocyte-culture toxicity assay system.
The compound extinction coefficient is ε [OD/M × cm] at the wavelength of maximum absorbency $\lambda_{max}$ [nm].

Throughout this application, various publications are referenced. The disclosures of these publications in their entireties are hereby incorporated by reference into this application in order to more fully describe the state of the art to which this invention pertains.

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

REFERENCES

1. Hearing V J Jr., "Monophenol monooxygenase (tyrosinase): Purification, properties, and reactions catalyzed." Methods Enzymol 142: 154-165, 1987.
2. Spritz R A et al., "Genetic-disorders of pigmentation," Adv Hum Genet 22: 1-45, 1994.
3. Frenk E, "Treatment of melasma with depigmenting agents." Melasma: New Approaches to Treatment, pp. 9-15. Martin Dunitz Ltd., London, 1995.
4. Dooley T P, "Is there room for a moderate level of regularity oversight?" In: Drug Discovery Approaches for Developing Cosmeceuticals: Advanced Skin Care and Cosmetic Products (Ed. Hori W), Chap. 1.4. International Business Communications, Southborough, Mass., 1997.
5. Dooley T P, "Topical skin depigmentation agents: Current products and discovery of novel inhibitors of melanogenesis." J. Dermatol. Treat. 8: 275-279, 1997.
6. Dooley T P, et al., "Development of an in vitro primary screen for skin depigmentation and antimelanoma agents." Skin Pharmacol. 7: 188-200, 1994.
7. Morse J L (Ed.), "An Abridgment of The New Funk & Wagnalls Encyclopedia," The Universal Standard Encyclopedia, Vol, 10, pp. 3662-3663. Unicorn, N.Y., 1955.
8. Budavari S (Ed.), "Gentisic acid," Merck Index, 11$^{th}$ Edn, Abstract No. 4290, p. 688. Merck & Co., Rahway, N.J., 1989.
9. J-Hua L, et al., "Direct analysis of salicylic acid, salicyl acyl glucuronide, salicyluric acid and gentisic acid in human plasma and urine by high-performance liquid chromatography." J. Chromatogr. [B] 675: 61-70, 1996.
10. Glatt H R, et al., "Multiple activation pathways of benzene leading to products with varying genotoxic characteristics." Environ Health Perspect 82: 81-89, 1989.
11. Glatt H R, "Endogenous mutagens derived from amino acids." Mutat Res. 238: 235-243, 1990.
12. La Du B N, "Alcaptonuria and ochronotic arthritis." Mol. Biol. Med. 8: 31-38, 1991.
13. Hearing V J, "Mammalian monophenol monooxygenase (tyrosinase): purification, properties, and reactions catalyzed." Methods Enzymol. 142: 154-65, 1987.
14. Spritz R A, et al., "Genetic disorders of pigmentation." Adv. Hum. Genet. 22: 1-45, 1994.
15. Hadley M E et al, "Melanotropic peptides for therapeutic and cosmetic tanning of the skin." NY Acad. Sci. 680: 424-39, 1993.
16. Sakai C et al, "Modulation of murine melanocyte function in vitro by agouti signal protein." EMBO J. 16: 3544-52, 1997.
17. Dooley T P, "Recent advances in cutaneous melanoma oncogenesis research." Onco. Res. 6: 1-9, 1994.
18. Bernmaman O, et al., "Treatment and camouflaging of pigmentary disorders." Clin. Dermatol. 6: 50-61, 1998.
19. Zaumseil R-P, et al., "Topical azelaic acid in the treatment of melasma: pharmacological and clinical considerations." In: Castanet J, Frenk E, Gaupe K et al (Eds) Melasma: new approaches to treatment. Martin Dunitz: London, pp 1640, 1995.
20. Schallreuter K U, "Epidermal adrenergic signal transduction as part of the neuronal network in the human epidermis." J. Invest Dermatol. 2: 3740, 1997.

21. Bennett D C, et al., "A line of non-tumorigenic mouse melanocytes, syngeneic with the B16 melanoma and requiring a tumour promoter for growth." Int. J. Cancer 349: 414-18, 1987.
22. Dooley T P et al., "Polyoma middle T abrogates TPA requirement of murine melanocytes and induces malignant melanoma." Oncogene 3: 531-6, 1988.
23. Brooks G et al., "Protein kinase C down-regulation, and not transient activation, correlates with melanocyte growth." Cancer Res. 51: 3281-8, 1991.
24. O'Keefe E, et al., "Cholera toxin mimics melanocyte stimulating hormone in inducing differentiation in melanoma cells." Proc. Natl. Acad. Sci. USA 71: 2500-4, 1974.
25. Curto, E. V., et al., "Inhibitors of Mammalian Melanocyte Tyrosinase: In Vitro Comparisons of Alkyl Esters of Gentisic Acid with Other Putative Inhibitors." Biochem. Pharmacol. 57: 663-672, 1999.
26. Sakurada, J., et al., "Kinetic and molecular orbital studies on the rate of oxidation of monosubstituted phenols and anilines by horseradish peroxidase compound II." Biochemistry 29: 4093-4098, 1990.
27. Arndt, et al., "The Pharmacology of Topical Therapy", Dermatology in General Medicine, 1987; T. B. Fitzpatrick, A. Z. Eisen, K. Wolff, I. M. Freedberg and K. F. Austen, eds., 3d ed., McGraw Hill, Inc., New York, pp. 2532-2540.
28. Lee, C. Y. and Whitaker, J. R. (Eds.) *Enzymatic Browning and its Prevention*. Pub. American Chemical Society, Washington, D.C., 1995.
29. Lerch, K "Tyrosinase: Molecular and active-site structure." In Lee, C. Y. and Whitaker, J. R. (Eds.) Enzymatic Browning and its Prevention. Pub. American Chemical Society, Washington, D.C., pp. 64-80, 1995.
30. Mishima, H., et al., "Fine structural demonstration of tyrosinase activity in the retinal pigment epithelium of normal and PTU-treated chick embryos." Albrecht Von Graefes Arch. Klin. Exp. Ophthalmol. 211: 1-10, 1979.
31. Deja, T. P., et al., "Demonstration of tyrosinase in the adult bovine uveal tract and retinal pigment epithelium." Invest Opthalmol. Vis. Sci. 17: 511-514, 1978.
32. Higashi, Y., et al., "Inhibition of tyrosinase reduces cell viability in catecholaminergic neuronal cells." J. Neurochem. 75: 1771-1774, 2000.

What is claimed is:

1. A method of reducing pigmentation of skin for cosmetic effects in a mammal comprising administering to the mammal an effective amount of a compound defined by structure (I), or a pharmaceutically acceptable salt or ester thereof:

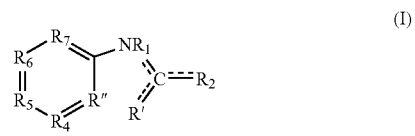

wherein:
a. $R_1$ is H or a valence for bonding;
b. $R_2$ is S, or SH;
c. one of the dotted lines ( - - - ) represents a bond;
d. $R_4$, $R_5$, $R_6$, and $R_7$ are independently $CR_8$;
e. $R_8$ is (i) hydrogen, (ii) halogen, (iii) $NO_2$, (iv) —CN, (v) —$OR_{10}$, (vi) —$NHSO_2$—$C_{1-3}$alkyl, (vii) —NHCO—$C_{1-5}$ alkyl, (viii) oxime, (ix) hydrazine, (x) —$NR_9R_{10}$, (xi) $HSO_2$, (xii) $HSO_3$, (xiii) thio-$C_{1-5}$ alkyl, (xiv) $C_{1-5}$ acyloxy, (xv) $H_2PO_3$, (xvi) thiol, (xvii) —$COOR_9$, (xviii) $C_{1-5}$ alkynyl, or (xix) —$C_{1-5}$ alkyl, —$C_{1-5}$ alkenyl, aryl, heteroaryl, or heterocycle, optionally substituted with one or more of —OH, —SH, C(O)H, $COOR_9$, $C_{1-5}$ acyloxy, halogen, $NR_9R_{10}$, $C_{1-5}$ thioether, or $C_{1-5}$ alkoxy;
f. $R_9$ is hydrogen or $C_{1-3}$ alkyl;
g. $R_{10}$ is hydrogen, or $C_{1-5}$ alkyl optionally substituted with —OH;
h. R" is CH or $CR_8$ and does not form a bond with R';
i. R' is $CH_3$ or $CH_2R_8$ and does not form a bond with R" or $R_7$.

2. The method of claim 1 wherein $R_4$, $R_5$, $R_6$, and $R_7$ are independently selected from $CR_8$, $R_8$ is $OR_9$, and 2 or 3 of $R_4$, $R_5$, $R_6$, and $R_7$ are CH.

3. The method of claim 1 wherein the compound has an $IC_{50}$ against mammalian tyrosinase activity of less than or equal to 300 uM.

4. The method of claim 1 wherein the compound has an $IC_{50}$ against melanin production in mammalian melanocytic cells of less than or equal to 300 uM.

5. The method of claim 1 wherein the compound absorbs ultraviolet radiation.

6. The method of claim 1 wherein the compound is an antioxidant.

7. The method of claim 1 wherein the mammal is a human.

8. The method of claim 1 wherein the administration is through a topical formulation or an occlusive patch.

9. The method of claim 1 wherein the method is for lightening skin pigmentation.

10. The method of claim 1 wherein the compound is thioacetanilide [$CH_3CSNHC_6H_5$].

* * * * *